US008501163B2

(12) United States Patent
Gierhart et al.

(10) Patent No.: US 8,501,163 B2
(45) Date of Patent: *Aug. 6, 2013

(54) PROTECTION AGAINST SUNBURN AND SKIN PROBLEMS WITH TOPICAL AND ORALLY-INGESTED DOSAGES OF ZEAXANTHIN

(75) Inventors: Dennis L. Gierhart, Chesterfield, MO (US); Joseph A. Fox, Chesterfield, MO (US)

(73) Assignee: ZeaVision LLC, Chesterfield, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/552,461

(22) Filed: Jul. 18, 2012

(65) Prior Publication Data
US 2012/0282204 A1 Nov. 8, 2012

Related U.S. Application Data

(60) Division of application No. 13/309,259, filed on Dec. 1, 2011, which is a continuation of application No. 10/356,134, filed on Feb. 1, 2003, now Pat. No. 8,088,363.

(60) Provisional application No. 60/421,518, filed on Oct. 28, 2002.

(51) Int. Cl.
*A61K 8/00* (2006.01)
(52) U.S. Cl.
USPC .............................. 424/59; 424/464; 514/763
(58) Field of Classification Search
USPC ............................................................ 424/59
See application file for complete search history.

(56) References Cited

U.S. PATENT DOCUMENTS

| | | | |
|---|---|---|---|
| 3,841,967 A | 10/1974 | Dasek et al. | 195/29 |
| 3,879,424 A | 4/1975 | Surmatis et al. | 260/340.9 |
| 3,891,504 A | 6/1975 | Schocher et al. | 195/28 R |
| 3,920,834 A | 11/1975 | Klaui et al. | 424/305 |
| 3,932,462 A | 1/1976 | Goetz et al. | 260/340.7 |
| 3,951,743 A | 4/1976 | Shepherd et al. | 195/28 R |
| 3,954,804 A | 5/1976 | Fischer et al. | 260/340.7 |
| 3,974,181 A | 8/1976 | Surmatis et al. | 260/340.9 |
| 4,078,094 A | 3/1978 | Katzen | 426/641 |
| 4,153,615 A | 5/1979 | Saucy | 260/340.9 R |
| 4,298,621 A | 11/1981 | Samis et al. | 426/55 |
| 4,405,417 A | 9/1983 | Grass et al. | 204/73 R |
| 4,522,743 A | 6/1985 | Horn et al. | 252/311 |
| 4,579,973 A | 4/1986 | Widmer et al. | 568/347 |
| 4,726,955 A | 2/1988 | Horn et al. | 426/73 |
| 4,851,339 A | 7/1989 | Hills | 435/67 |
| 4,935,409 A | 6/1990 | Wollweber et al. | 514/63 |
| 4,952,716 A | 8/1990 | Lukac et al. | 556/482 |
| 5,180,747 A | 1/1993 | Matsuda | 514/681 |
| 5,227,507 A | 7/1993 | Lukac et al. | 556/449 |
| 5,242,950 A | 9/1993 | Fries Hastings | 514/654 |
| 5,290,605 A | 3/1994 | Shapira | 424/439 |
| 5,308,759 A | 5/1994 | Gierhart | 435/67 |
| 5,310,764 A | 5/1994 | Baranowitz et al. | 514/725 |
| 5,350,773 A | 9/1994 | Schweikert et al. | 514/763 |
| 5,356,636 A | 10/1994 | Schneider et al. | 424/489 |
| 5,360,730 A | 11/1994 | Orndorff et al. | 435/257.1 |
| 5,382,714 A | 1/1995 | Khachik | 568/834 |
| 5,386,063 A | 1/1995 | Khachik et al. | 568/494 |
| 5,427,783 A | 6/1995 | Gierhart | 424/93.4 |
| 5,429,939 A | 7/1995 | Misawa et al. | 435/67 |
| 5,437,997 A | 8/1995 | Liao et al. | 435/257.1 |
| 5,523,494 A | 6/1996 | Torres-Cardona et al. | 568/834 |
| 5,527,533 A | 6/1996 | Tso et al. | 424/422 |
| 5,607,839 A | 3/1997 | Tsubokura et al. | 435/67 |
| 5,684,238 A | 11/1997 | Ausich et al. | 800/205 |
| 5,773,026 A | 6/1998 | Schlipalius | 424/450 |
| 5,777,173 A | 7/1998 | Paust et al. | 568/366 |
| 5,780,693 A | 7/1998 | Bernhard et al. | 568/816 |
| 5,871,766 A | 2/1999 | Hennekens | 424/422 |
| 6,110,478 A | 8/2000 | Harang | 424/401 |
| 6,218,436 B1 | 4/2001 | Howard et al. | 514/725 |
| 6,254,898 B1 | 7/2001 | Bragaglia | 424/729 |
| 6,296,880 B1 | 10/2001 | Murad | 424/616 |
| 6,368,621 B1 | 4/2002 | Engel et al. | 424/451 |
| 6,383,523 B1 | 5/2002 | Murad | 424/616 |

FOREIGN PATENT DOCUMENTS

| | | |
|---|---|---|
| EP | 0 747 483 A2 | 12/1996 |
| FR | 2 339 403 A1 | 8/1977 |
| WO | WO 96/40092 A1 | 12/1996 |
| WO | WO 97/16175 A1 | 5/1997 |
| WO | WO 01/17519 A1 | 3/2001 |
| WO | WO 03/070203 A1 | 8/2003 |

OTHER PUBLICATIONS

Alaluf S, et al, "Dietary carotenoids contribute to normal human skin color and UV photosensitivity," J Nutr. Mar. 2002; 132(3): 399-403.
Alpers, J.R., et al, "Serum Carotenoids and Age-Related Macular Degeneration," Invest Ophthalmol Vis Sci 36: S9 (1995).
Andreassi L, et al, "Measurement of cutaneous colour and assessment of skin type," Photodermatol Photoimmunol Photomed. Feb. 1990; 7(1): 20-4.
AREDS Research Group, Report No. 8, "A randomized, placebo-controlled, clinical trial of high-dose supplementation with vitamins C and E, beta carotene, and zinc for age-related macular degeneration and vision loss," Arch Ophthalmol 119: 1417-1436 (2001).

(Continued)

Primary Examiner — Jake M. Vu
(74) Attorney, Agent, or Firm — Nixon Peabody LLP

(57) ABSTRACT

A carotenoid substance called zeaxanthin, when ingested orally at suitable dosages, can provide effective protection against sunburns and darken the skin to emulate a healthy suntan. Zeaxanthin may induce: (i) a mild but noticeable tinting, shading, or darkening of skin color, comparable to a mild suntan; (ii) a substantial increase in the person's ability to withstand elevated levels of sun or UV exposure; and, (iii) an increased ability of reddened and sunburned skin to convert into intact skin that looks browned and healthily tanned. Topical formulations containing zeaxanthin can be administered to the skin during the time period of ingesting the oral formulation to further protect the skin and provide an additional darkening of the skin.

17 Claims, 1 Drawing Sheet

(56) References Cited

OTHER PUBLICATIONS

Ascherio, A., et al, "Correlations of Vitamin A and E Intakes with the Plasma Concentrations of Carotenoids and Tocopherols among American Men and Women," J of Nutrition 122 (9): 1792-1801 (1992).
Badminton MN, et al, "Management of acute and cutaneous porphyrias," Int J Clin Pract. May 2002; 56(4): 272-8.
Bendich, A., et al, "Biological actions of carotenoids," FASEB Journal 3: 1927-1932 (1989).
Bertram, J.S., et al, "Diverse carotenoids protect against chemically induced neoplastic transformation," Carcinogenesis 12 (4): 671-678 (1991).
Biesalski HK, et al, "UV light, beta-carotene and human skin - beneficial and potentially harmful effects," Arch Biochem Biophys. May 1, 2001; 389(1): 1-6.
Black HS, et al, "Protective role of butylated hydroxytoluene and certain carotenoids in photocarcinogenesis," Photochem Photobiol. May 1991; 53(5): 707-16.
Blumenkranz, M.S., et al, "Risk factors in age-related maculopathy complicated by choroidal neovascularization," Ophthalmology 93: 552-558 (1986).
Bohm F, et al, "Enhanced protection of human cells against ultraviolet light by antioxidant combinations involving dietary carotenoids," J Photochem Photobiol B. Jul. 31, 1998; 44(3): 211-5.
Bone R.A., et al, "Stereochemistry of the macular carotenoids," Invest. Ophthalmol. Vis. Sci. 34: 2033-2040 (1993).
Bone, R.A., "The role of the macular pigment in the detection of polarized light," Vision Research 30: 213-220 (1979).
Bone, R.A., et al, "Analysis of the macular pigment by HPLC: retinal distribution and age study," Invest Ophthalmol Vis Sci 29: 843-9 (1988).
Bone, R.A., et al, "Distribution of macular pigment stereomers in individual eyes, including those with age-related macular degeneration (AMD)," Arvo Abstracts Invest Ophthalmol Vis Sci V.35: 4 pp. 1502 (1994).
Bone, R.A., et al, "Preliminary identification of the human macular pigment," Vision Res. 25: 1531-1535 (1985).
Bowmaker, J.D., et al, "Visual pigments and oil droplets in genetically manipulated and carotenoid deprived quail: a microspectrophotometric study," Vision Res 33: 571-578 (1993).
Burton, G.W., "Antioxidant action of carotenoids," American Institute of Nutrition, 109-111 (1988).
Castorina, C., et al, "Lipid peroxidation and antioxidant enzymatic systems in rat retina as a function of age," Neurochem Res 17(6): 599-604 (1992).
Christen, W.G., "Antioxidants and eye disease," The Amer J of Medicine 97 (suppl 3A): 3A-142-3A-162 (1994).
Columbo, V.E., et al, "Structures and properties of stabilized vitamin and carotenoid dry powders," Food Structure 10: 161-170 (1991).
Conn, P.F., et al, "The singlet oxygen and carotenoid interaction," J Photochem Photobiol B Biol 11: 41-47 (1991).
Crary, E.J., "Antioxidant treatment of macular degeneration of the aging and macular edema in diabetic retinopathy," Southern Med J 80: 38 (1997).
di Mascio, P., et al, "Antioxidant defense systems: the role of carotenoids, tocopherols, and thiols," Am. J. Clin. Nut. 53: 194S-200S (1991).
di Mascio, P., et al, "Lycopene as the most efficient biological carotenoid singlet oxygen quencher," Archives of Biochemistry and Biophysics 274: 532-538 (1989).
"Do Antioxidants prevent or Retard the Onset of AMD?", J. Amer. Osteopathic Assn. 95(1): 26 (Jan. 1995).
Dorey, C.K., et al, "Lipofuscin in aged and AMD eyes," in Retinal Degeneration (Hollyfield et al., editors, Plenum Press, New York, 1993).
Eichler O, et al, "Divergent optimum levels of lycopene, beta-carotene and lutein protecting against UVB irradiation in human fibroblasts," Photochem Photobiol. May 2002; 75(5): 503-6.
Eye Disease Case Control Study Group, "Antioxidant status and neovascular age-related macular degeneration," Arch. Ophthalmol. 11: 104-109 (1993).
Fite, K.V., "Drusen-like deposits in the outer retina of Japanese quail," Exp Eye Res 59: 417-424 (1994).
Fite, K.V., et al, "Age, sex and light damage in the avian retina: a model system," P. Bagnoli et al, Ed, The Changing Visual System: 283-294 (1991).
Fite, K.V., et al, "Experimental light damage increases lipofuscin in the retinal pigment epithelium of Japanese quail," Exp Eye Res 57: 449-460 (1993).
"Flora-Glo Lutein" product specification sheets (Kemin Industries Inc., Des Moines, Iowa, 1997).
Foote, C.S., et al, "Chemistry of singlet oxygen. X. Carotenoid quenching parallels biological protection," J Amer Chem Soc 92: 17 (1970).
Fung TT, et al, "Vitamin and carotenoid intake and risk of squamous cell carcinoma of the skin," Int J Cancer. Jan. 1, 2003; 103(1): 110-5.
Gerster, H., "Review: antioxidant protection of the aging macula," Age and Aging 20: 60-69 (1991).
Goldberg, J., et al, "Factors Associated with Age-Related Macular Degeneration: An analysis of Data from the First National Health and Nutrition Examination Survey," Am J Epidemiol 128(4): 700-10 (1988).
Gonzalez S, et al, "Dietary lutein/zeaxanthin decreases ultraviolet B-induced epidermal hyperproliferation and acute inflammation in hairless mice," J InvestDermatol. Aug. 2003; 121(2): 399-405.
Gottsch, J.D., et al, "Hematogenous photosensitization," Inves Opthamol & Vis Sci 31(9): 1674-1682 (1990).
Gruszecki, W.I., et al, "Orientation of xanthophylls in phosphatidylcholine multibilayers," Biochim Biophys Acta 1023(3): 405-412 (1990).
Haegerstrom-Portnoy, G., "Short-wavelength-sensitive-cone sensitivity loss with aging: a protective role for macular pigment?," J. Opt. Soc. Am. A5: 2140-2144 (1988).
Ham, W.T., et al, "Basic mechanisms underlying the production of photochemical lesions in the mammalian retina," Curr Eye Res 3(1): 165-174 (1984).
Ham, W.T., et al, "The photopathology and nature of the blue-light and near-UV retinal lesions produced by lasers and other optical sources," ed. Plenum Press; New York, Laser Application in Medicine and Biology: 191-246 (1989).
Hammond, B.R., "The Relationship Between Cigarette Smoking and Peak Macular Pigment Density," Invest. Opthalm. Visual Sci. 36(4): S233 (Conference Proceedings, Mar. 15, 1995).
Handelman, G.J. and Dratz, E.A., "The role of antioxidants in the retina and retinal pigment epithelium and the nature of prooxidant-induced damage," Adv. in Free Radical Biology & Medicine 2: 1-23 and 55-57 (1986).
Handelman, G.J., et al, "Carotenoids in the human macula and whole retina," Invest. Ophthalmol. Vis. Sci. 29: 850-855 (1988).
Hata TR, et al, "Non-invasive raman spectroscopic detection of carotenoids in human skin" J Invest Dermatol. Sep. 2000; 115(3): 441-8.
Heinrich U et al, "Supplementation with β-carotene or a similar amount of carotenoids protects humans from UV-induced erythema," J Nut. 2003 133: 98-101.
Hockwin, O., et al, "Investigations on lens transparency and its disturbances by microdensitometric analyses of Scheimpflug photographs," Curr Eye Res 3(1): 15-22 (1984).
Hope, G.M., et al, "A primate model for age related macular drusen," British J of Ophthalmol 76: 11-16 (1992).
Jampol, L.M., "Antioxidants, zinc, and age-related macular degeneration," Arch Ophthalmol 119: 1533-1534 (2001).
Kahn, H.A., et al, "Framingham Eye Study 1. Outline and major prevalence finding," Am J Epidemiol 106(1): 17-32 (1977).
Kang S, et al, "Photoaging: pathogenesis, prevention, and treatment," Clin Geriatr Med. Nov. 2001; 17(4): 643-59, v-vi.
Karagas MR, at el, "Risk of squamous cell carcinoma of the skin in relation to plasma selenium, alpha-tocopherol, beta-carotene, and retinol: a nested case-control study," Cancer Epidemiol Biomarkers Prev. 6(1): 25-9 (1997) (abstract).

Khachik F., et al, "Separation and identification of carotenoids and their oxidation products in the extracts of human plasma," Anal Chem 64: 2111-22 (1992).

Khachik, F., et al, "Lutein, lycopene, and their oxidative metabolites in chemoprevention of cancer," J of Cell Biochem S22: 236-246 (1995).

Kirschfeld, K., "Carotenoid pigments: their possible role in protecting against photooxidation in eyes and photoreceptor sells," Proc R Soc London B 216: 71-85 (1982).

Klaui, H. and Bauerenfeind, C.J., pp. 86-102 in Carotenoids as colorants and vitamin A precursors, Baurenfeind, C.J., Ed, Academic Press (1981).

Klein, B., et al, "Prevalence of Age-related Lens Opacities in a Population: The Beaver Dam Eye Study," Ophthalmol 99(4): 546-52 (1992).

Klein, R., et al, "Racial/ethnic differences in age-related maculopathy. Third National Health and Nutrition Examination Survey," Opthamology 102(3): 371-81 (1995).

Landrum, J.T., et al, "Macular Pigment Stereomers in Individual Eyes: A Comparison Between Normals and Those With Age-Related Macular Degeneration" (abstract), *Invest. Opthalm. Visual Sci.* 36(4): S895 (Conference Proceedings, Mar. 15, 1995).

Lee EH, et al, "Dietary lutein reduces ultraviolet radiation-induced inflammation and immonosuppression," J Invest Dermatol Feb. 2004; 122(2): 510-7.

Lee J, et al, "Carotenoid supplementation reduces erythema in human skin after simulated solar radiation exposure," Proc Soc Exp Biol Med. Feb. 2000; 223(2): 170-4.

Malinow, M.R., et al, "Diet-related macular anomalies in monkeys," Invest. Ophthalmol. Vis. Sci. 19: 857-863 (1980).

Mangels, A.R., et al, "Carotenoid content of fruits and vegetables: an evaluation of analytical data," J Amer Diet Assn 93(3): 284-96 (1993).

Mares-Perlman, J.A., et al, "Serum antioxidants and age-related macular degeneration in a population-based case-control study," Arch Ophthalmol 113: 1518-1523 (1995).

Mathews-Roth MM, "Therapeutic uses of carotenoids in skin photosensitivity diseases," in Krinsky, NI, et al, editors, *Carotenoids in Health and Disease* (Marcel Dekker, 2004).

Millen AE, et al, "Diet and melanoma in a case-control study. Cancer Epidemiol Biomarkers," Prey. Jun. 2004; 13(6): 1042-51.

Monaco, W.A., et al, "The rhesus monkey as an animal model for age-related maculopathy," Optometry Vis Sci 67(7): 532-537 (1990).

Mukhtar H, "Eat Plenty of Green Leafy Vegetables for Photoprotection: Emerging Evidence," J Invest Dermatol 121: 399-405 (2003).

National Advisory Eye Council, Vision Research: A National Plan, 1994-1998 (NIH Publication 93/3186), pp. 55-64, 336, and 356(1998).

National Eye Advisory Council, pp. 13-38 in Vision Research—A National Plan: 1999-2003 (NIH Publ. 99/4120, 1999).

Niki E, et al, "Interaction among vitamin C, vitamin E, and beta-carotene," Am J Clin Nut. Dec. 1995; 62(6 Suppl): 1322S-1326S.

Nishino H, et al, "Cancer prevention by natural carotenoids," Biofactors. 2000; 13(1-4): 89-94.

Nussbaum, J.J., et al, "Historic perspectives Macular yellow pigment. The first 200 years," Ophthal Comm Soc 1(4): 296-310 (1981).

O'Connor, et al, "Modulation of UVA light-induced oxidative stress by beta-carotene, lutein and astaxanthin in cultured fibroblasts," J Dermatol Sci Mar. 1998; 16(3): 226-30.

Offord EA, et al, "Photoprotective potential of lycopene, beta-carotene, vitamin E, vitamin C and carnosic acid in UVA-irradiated human skin fibroblasts," Free Radic Biol Med. Jun. 15, 2002; 32(12): 1293-303.

Parker, R.S., "Carotenoids in human blood and tissues," Amer Inst Nutr: 101-104 (1988).

Sanders, T.A.B., et al, "Essential fatty acids, plasma cholesterol, and fat-soluble vitamins in subjects with age-related maculopathy and matched control subjects," Am J Clin Nutr 57: 428-433 (1993).

Saurat JH, "Skin, sun, and vitamin A: from aging to cancer," J Dermatol. Nov. 2001; 28(11): 595-8.

Schalch, W., "Carotenoids in the retina—a review of their possible role in preventing or limiting damage caused by light and oxygen," Emerit I., et al, Ed, Free Radicals and Aging: 280-298 (1992).

Seddon, J.M., et al, "Dietary carotenoids, vitamins A, C, and E, and advanced age-related macular degeneration," JAMA 272: 1413-1420 (1994).

Seddon, J.M., et al, "Vitamins, minerals, and macular degeneration: Promising but unproven hypotheses," Arch Ophthalmol 112: 176-179 (1994).

Snodderly, D.M., "Evidence for protection against age-related macular degeneration by carotenoids and antioxidant vitamins," Am J Clin Nutr 62(Suppl): 1448S-61S (1995).

Snodderly, D.M., et al, "Distribution of individual macular pigment carotenoids in central retina of macaque and squirrel monkeys," Invest Ophthalmol Vis Sci 32(2): 268-279 (1991).

Snodderly, D.M., et al, "The macular pigment. I. Absorbance spectra, localization, and discrimination from other yellow pigments in primate retinas," Invest Ophthalmol Vis Sci 25: 660-673 (1984a).

Snodderly, D.M., et al, "The macular pigment. II. Spatial distribution in primate retinas," Invest Ophthalmol Vis Sci 25: 674-85 (1984b).

Sperduto, R.D., et al, "Do we have a nutritional treatment for age-related cataract or macular degeneration?," Arch. Ophthalmol. 108: 1403-1405 (1990).

Stahl W, et al, "Carotenoids and carotenoids plus vitamin E protect against ultraviolet light-induced erythema in humans," Am J Clin Nutr. Mar. 2000; 71(3): 795-8.

Stahl W, et al, "Carotenoids in systemic protection against sunburn," in Krinsky, NI, et al, editors, *Carotenoids in Health and Disease* (Marcel Dekker, 2004).

Stahl W, et al, "Dietary tomato paste protects against ultraviolet light-induced erythema in humans," J Nutr. May 2001; 131(5): 1449-51.

Stahl W, et al, "Increased dermal carotenoid levels assessed by noninvasive reflection spectrophotometry correlate with serum levels in women ingesting Betatene," J Nutr. May 1998; 128(5): 903-7.

Stone, W.L., et al, "A reinvestigation of the fatty acid content of bovine, rat and frog retinal rod outer segments," Exp Eye Res 28: 387-397 (1979).

Sunness, J.S., et al, "Diminished foveal sensitivity may predict the development of advanced age-related macular degeneration," Ophthalmol 96(3): 375-381 (1989).

Taylor, A., et al, "Oxidation and aging: impact on vision," Journal of Toxicology and Industrial Health 9:349-371 (1993).

Taylor, H.R., et al, "The long-term effects of visible light on the eye," Arch Ophthalmol 110: 99-104 (1992).

"The Effect of a Dietary Lack of Xanthophyll on the Eye of the Monkey," *Nutrition Reviews* 38: 384-386 (1980).

Thylefors, B., et al, "Global Data on Blindness," Bulletin of the World Health Organization 73(1): 115-121 (1995).

US Food and Drug Administration, "Tanning Pills" (official public warning notice, Oct. 18, 2000), www.cfsan.fda.gov/-dms/cos-tan2.html.

US Food and Drug Administration, "Warning letters cite cosmetics as adulterated due to violative use of the color additive canthaxanthin" (Jan. 4 and Apr. 5, 2005), www.cfsan.fda.gov/-dms/coscanth.html.

van Dam RM, et al, "Diet and basal cell carcinoma of the skin in a prospective cohort of men," Am J Clin Nut. Jan. 2000; 71(1): 135-41.

Vingerling, J.R., "Epidemiology of age-related maculopathy," Epidemiol Rev 17(2): 347-360 (1995).

Weiser, J., et al, "Provitamin A activities and physiological functions of carotenoids in animals: relevance to human health," Ann NY Acad Sci 691: 213-215 (1993).

Weiter, J.J., et al, "Central sparing in annular macular degeneration," Am J Ophthalmol 106: 286-292 (1988).

Werner, J.S., "Aging and human macular pigment density," Vis Res 27(2): 257-268 (1987).

West, S., et al, "Are antioxidants or supplements protective for age-related macular degeneration?," Arch Ophthalmol 112: 222-227 (1994).

West, S., et al, "Epidemiology of risk factors for age-related cataracts," Survey Ophthalmol 39(4): 323-34 (1995).

Westerhof W, et al, "The relation between constitutional skin color and photosensitivity estimated from UV-induced erythema and pigmentation dose-response curves," J Invest Dermatol. Jun. 1990; 94(6): 812-6.

Widmer et al, "Technical Procedures for the Synthesis of Carotenoids and Related Compounds from 6-Oxo-Isophrone: Synthesis of (3R-3'R) Zeaxnathin" Helvetica Chemica Acta, 73, 861-867 (1990).

Wingerath T, et al, "Xanthophyll esters in human skin," Arch Biochem Biophys. Jul. 15, 1998; 355(2): 271-4.

Wolf C, et al, "Do oral carotenoids protect human skin against ultraviolet erythema, psoralen phototoxicity, and ultraviolet-induced DNA damage?", J Invest Dermatol. 90(1): 55-7 (1988) (abstract).

Supplemental European Search Report for European Application No. 04 70 7393, dated Nov. 9, 2010 (3 pages).

Boelsma E, et al, Nutritional Skin Care: Health Effect of Micronutrients and Fatty Acids,: The American Journal of Clinical Nutrition, American Society for Nutrition, US, vol. 73, Jan. 1, 2001 (12 pages).

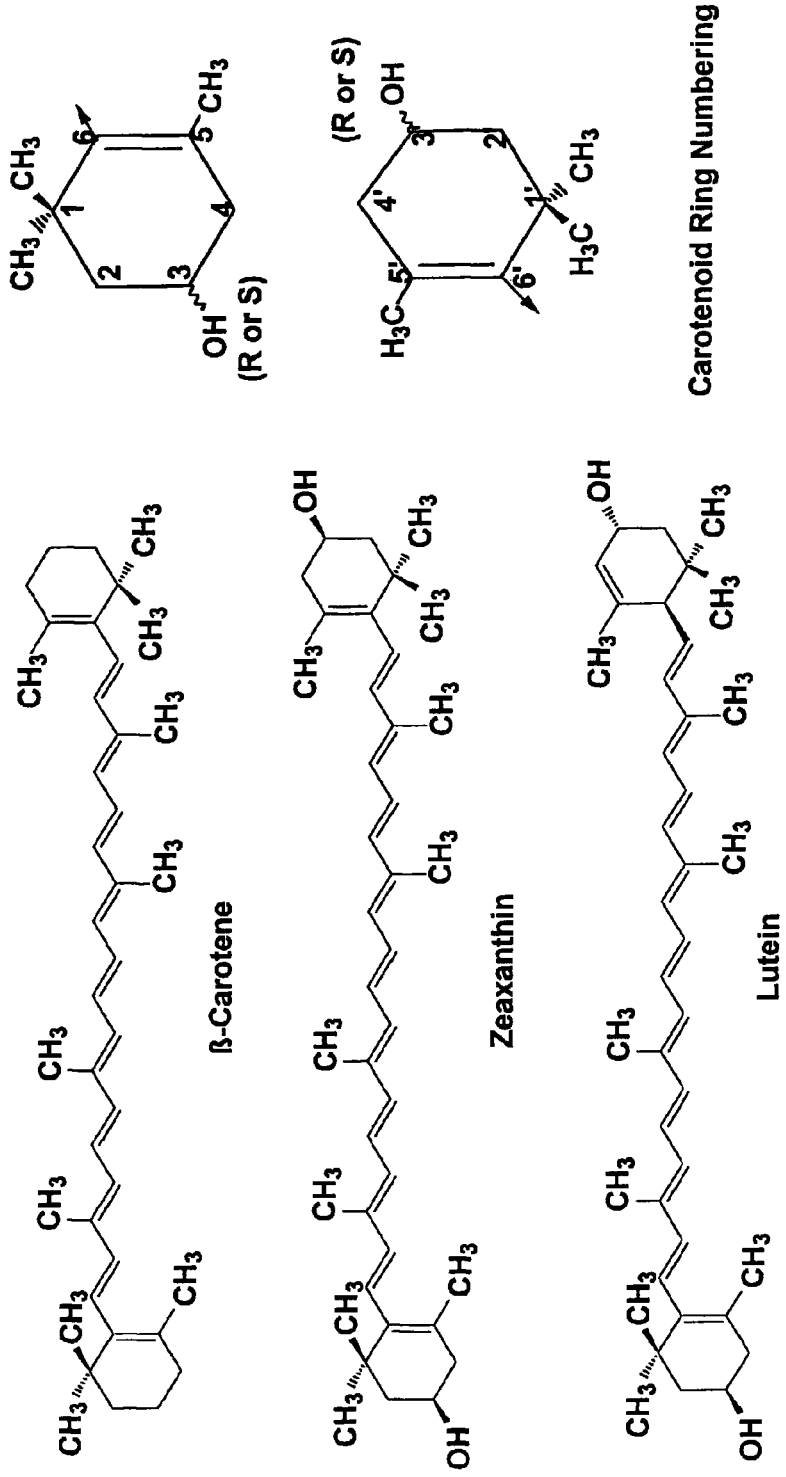

PROTECTION AGAINST SUNBURN AND SKIN PROBLEMS WITH TOPICAL AND ORALLY-INGESTED DOSAGES OF ZEAXANTHIN

CROSS REFERENCE TO RELATED APPLICATIONS

This application is a divisional of U.S. patent application Ser. No. 13/309,259, titled "Protection Against Sunburn And Skin Problems With Orally-Ingested High-Dosage Zeaxanthin," filed on Dec. 1, 2011, which is a continuation of U.S. patent application Ser. No. 10/356,134, titled "Protection Against Sunburn And Skin Problems With Orally-Ingested High-Dosage Zeaxanthin," now issued as U.S. Pat. No. 8,088,363, filed on Feb. 1, 2003, which is related to and claims priority to U.S. Provisional Application No. 60/421,518, titled "Protection Against Sunburn And Skin Problems With Orally-Ingested High-Dosage Zeaxanthin," filed on Oct. 28, 2002, each of which being incorporated herein in its entirety.

BACKGROUND OF THE INVENTION

This invention is in the field of biochemistry, pharmacology, and nutritional supplements, and relates to a new use for zeaxanthin, a carotenoid found in plants such as spinach, kale, and corn.

Numerous efforts have been made to identify drugs or other biomolecules that can be orally ingested and that will safely accomplish either or both of the following: (i) cause a darkening of the color (also referred to as tint, tone, pigmentation, or similar terms) of the skin, in a manner that looks like a healthy and natural suntan, while reducing or eliminating the need to spend hours in direct sunlight or in front of ultraviolet lamps; and/or, (ii) reduce the risk of a sunburn, such as when the summer season is approaching, and when someone is planning a vacation, golf or fishing outing, a ski trip, or some other activity or travel that will likely result in substantially more sun exposure than a person has had over the preceding month or two.

If either of these effects could be provided, safely and effectively, by a compound that could be put in a bottle, the value and benefits would be very large, both for cosmetic and commercial reasons, and for medical reasons as well. It is well known that overexposure to direct sunlight causes and accelerates premature aging and wrinkling of skin. It has also been shown that if a person suffers several serious sunburns (especially when young), it will increase that person's risk of skin cancer (including melanoma, an extremely malignant and deadly cancer) later in life. In addition, because of ozone depletion in the upper atmosphere, both of these risks are likely to accelerate and become worse in the future, since the ozone layer plays a crucial role in reducing and controlling the amount of skin-damaging ultraviolet rays that reach the earth's surface.

In addition, it is also likely that if people could obtain a "pre-season suntan", they might also get more exercise, and would be healthier as a result, since having an overly pale and "pasty" appearance tends to discourage people from getting involved in outdoor activities with other people.

It also is known that various types of drugs (such as quinoline antibiotics, as just one example) can create a condition of hypersensitivity to sunlight, which will increase the risk of sunburns and other skin problems. Accordingly, if someone is taking (or is planning to take) a therapeutic drug which will create that type of side effect, it would be highly useful if a second agent were available which could mitigate the skin-related or sun-related side effects of the therapeutic drug.

In addition, some people suffer from diseases or syndromes in which their skin is abnormally sensitive and vulnerable to sunburns, or to the formation of uneven or discolored patches (often called blotches or splotches) that go beyond the normal formation of freckles, or other types of discomfort or lesions, when people who suffer from these diseases or syndromes have their skin exposed to direct sunlight. One class of such diseases, which involve defects in the biosynthesis or metabolism of heme (the protein that complexes with iron to make hemoglobin), is generally referred to as porphyrias; this cluster of diseases is subdivided into at least a dozen named subclasses, such as "erythropoietic protoporphyria", etc. Another class of diseases or syndromes which render some people abnormally vulnerable to skin damage by sun involves the trait of albinism, in which people have abnormally pale skin due to low quantities of melanin, the dark brown or black pigment that normally occurs in skin and various other tissues. It is anticipated that orally-ingested zeaxanthin as disclosed herein may be able to help mitigate at least some of these types of skin diseases or syndromes, as can be evaluated through routine trials on patients who suffer from any such disease or syndrome.

It should be noted that the term "skin" as used herein refers to epidermal layers (including surface layers, as well as near-surface layers that can be affected by sunburns), in any one or more areas of the body, head, or limbs (including areas of the scalp, etc). As will be recognized by anyone skilled in the art, the primary areas of concern are those areas that are or may be exposed to sunlight or other UV radiation, and if any significant level of additional protection to any one or more of those areas can be provided by zeaxanthin treatments disclosed herein, that is deemed to be a valuable result. As just one example, a golfer or fisherman (or anyone else) is likely to have his forearms, nose, forehead, and other areas exposed to sufficient sunlight, during the spring and early summer, to build up a sufficient tan in those areas to prevent any substantial burning, during normal activities. However, after a day at a beach, pool, lake, golf course, or other such area, that person may suffer a severe sunburn on his feet, or the tops of his ears (after a recent haircut), or some other area that is normally covered by clothing or hair, and those types of severe sunburns can cause both serious pain, as well as increased risks of skin cancer, premature aging, and other problems. Accordingly, the zeaxanthin treatments disclosed herein can be used to protect against such "limited area" burns or damage.

The term "skin" does not include epithelial surfaces, which are commonly referred to as mucous membranes, and which notably includes the lips (which occasionally suffer from sunburns that can be very painful due to the large numbers of nerve endings in and near the lips). None of the test subjects reported in the Examples suffered any sunburns on their lips, while taking zeaxanthin, and it is believed likely that zeaxanthin ingestion as disclosed herein can provide at least some level of increased protection against UV damage, for the lips and other epithelial surfaces. However, that likelihood has not yet been evaluated by any tests that focus specifically on epithelial surfaces.

At the current time, most efforts to create "suntan in a bottle" compounds that have a reached actual commercialization and public use involve lotions, creams, and similar "topical" agents that are applied directly to a surface of the skin. Examples of agents which are used in such lotions and other topical formulas include dihydroxyacetone, erythrulose, and tyrosine. Such topical formulations can be used in conjunction with "systemic" (i.e., orally-ingested) tanning agents, including the zeaxanthin-containing oral formulations disclosed herein. While the present invention is principally directed to oral dosages of zeaxanthin, as will be discussed below, it should be noted that zeaxanthin can also be added to a tanning lotion or other topical formulation, to achieve beneficial results.

The principal focus of this invention relates to orally-ingested formulations. Such orally-ingested formulations are referred to herein as "oral tanning" agents, compounds, products, or formulations. For convenience, they are also referred to herein simply as tanning agents (or compounds, formulations, etc.), with the understanding that the class of tanning agents being referred to herein are limited to agents that are designed and formulated to be orally ingested, unless a particular reference refers to a topical formulation such as a lotion. Since various lotions and other topical formulations are already commercially available for imparting a darker tint if applied directly to the skin, the primary value of the discovery disclosed herein appears to reside in its disclosure of a truly safe yet effective and potent agent that, when taken orally, can protect skin against sunburn and certain other types of skin problems, regardless of whether any lotions or other topical formulations are also used.

It also should be noted that the term "photoprotective" is frequently used to refer to agents that can protect against sunburn, create or enhance tans, etc. However, that term is not favored or used herein, since it is too broad and non-specific, and can include every type of formulation discussed herein, plus a wide range of other agents as well (including hats, sunglasses, conventional sunblocking and SPF-rated suntan lotions, and opaque ointments and creams). Many types of "photoprotective" agents are intended simply to block the harmful rays of the sun. By contrast, this invention discloses an oral agent that can treat the skin in a manner that will lead to a change in pigmentation and/or antioxidant concentration within and/or beneath the skin, in a manner which will render the skin better-prepared to deal with direct sunlight, thereby reducing the risk and/or severity of skin problems such as sunburns, premature wrinkling and aging, skin cancer, etc.

On the subject of orally-ingested tanning agents, it should be noted that various types of pills are sold with labels and advertisements suggesting that those pills may be able to help accelerate or promote tanning. However, the only such orally ingestible agent that actually works effectively for that purpose contains canthaxanthin, which has been declared illegal for tanning purposes because of a type of damage that was observed in the retina when high dosages were ingested (as discussed in more detail below). Other agents, such as tyrosine (an amino acid that is a precursor of melanin) are only marginally effective at best, and are generally dismissed as being ineffective, in reviews and analyses that are available on websites such as http://www.sunless.com/safe/tanning-pillsdontwork.php. However, it should be noted that research is being done on other agents, most notably including "melanocyte-stimulating hormone" (MSH) and various analogs or active fragments thereof, which are not currently available to the public, but which may become available someday.

Roughly 20 years ago, a class of compounds called "carotenoids" was recognized as having good potential as orally-ingested tanning agents, because of the biological roles and effects of carotenoids in nature. Very briefly, carotenoids are large organic molecules that have numerous double bonds between carbon atoms; the chemical structures of several important carotenoid molecules are shown in the enclosed FIG. 1.

The alternating pattern of double and single bonds shown in FIG. 1 is the conventional structure shown in drawings to represent carotenoids. However, because of the clustering of these double bonds, the electrons that surround the straight-chain portion of these carotenoids actually form a fluid-like and movable network that resembles the "resonating" or "electron cloud" structures of aromatic rings such as benzene. This "resonating" system of interacting electrons in a movable cloud allows carotenoids to absorb UV light very efficiently, without being destroyed. In a sense, this absorbing action is analogous to a boxing glove punching a foam rubber pillow, rather than a wooden board; because the pillow can flex, adapt, and adjust to the impact, it will not be broken, even by a blow that would easily break a wooden board. And, just as a pillow can absorb the force of a blow from a boxing glove, when a carotenoid molecule absorbs the energy of a UV photon, it prevents the UV photon from damaging other biomolecules (such as DNA or proteins).

On the subject of conjugation, it should be noted that zeaxanthin has a higher degree of conjugation than lutein. As shown in FIG. 1, the conjugated (and therefore resonant) electron structure of zeaxanthin extends into both of the end rings. That does not occur with lutein, which is non-symmetric, and which has a non-conjugated end ring.

On the subject of comparative structures, it also should be noted from FIG. 1 that zeaxanthin has a hydroxy group on each of its end rings, while β-carotene does not have either of those two groups. As is well known to chemists, when hydroxy groups are added to an organic structure, they tend to make that structure more polar, and more soluble in water. Since the two hydroxy groups on zeaxanthin are positioned on its end rings, they tend to give zeaxanthin better "membrane-spanning" traits than β-carotene (as well as certain other types of positioning and interacting traits, in aqueous and cellular systems).

It should also be kept in mind that after β-carotene is ingested, one of its predominant fates is to be cleaved in half, so that the two halves can be used to make Vitamin A and other retinoid molecules. That apparently does not happen with zeaxanthin. Therefore, ingested zeaxanthin appears to be capable of lasting and enduring, in a mammalian body, for substantially longer periods of time than β-carotene.

Because of their extremely useful roles as UV absorbers, and also as anti-oxidants (as discussed below), carotenoids evolved over the eons to play very important roles in plant leaves, and in bacteria that must grow in direct and prolonged sunlight.

As indicated above, carotenoids are pigment molecules. Their colors are generally red, orange, or yellow, because those are the color ranges that remain and are reflected outwardly, when light in the blue and ultraviolet region of the spectrum is absorbed by the carotenoid molecules. When the leaves of trees or bushes turn red, orange, and yellow in the fall, those colors are due mainly to carotenoids, which become the dominant pigments in the leaves after chlorophyll production slows down because of cold weather, and after any chlorophyll that still remains in the leaves when cold weather arrives is gradually degraded.

In addition to being pigments that can absorb ultraviolet radiation, carotenoids also are potent anti-oxidant compounds. This means that they can "scavenge" or "quench" certain types of highly reactive and damaging molecules called "oxygen free radicals". Oxygen free radicals are commonly created when a photon of UV light breaks apart a biological molecule that contains oxygen, in a manner that creates a single "unshared electron" on one surface of the oxygen atom. Because oxygen free radicals are highly unstable and reactive, they pose a serious danger of randomly attacking and damaging nearly any type of biological molecule or membrane. Therefore, the ability of carotenoid molecules to absorb and "quench" oxidative free radicals played a very important and useful contributory role in the evolution of carotenoid molecules as one of the primary natural defenses against UV damage in plants, and among bacteria that must be able to withstand direct sunlight for hours.

As mentioned above, by the early 1980's, carotenoids were recognized as being potentially useful as orally-ingested tanning agents, for two main reasons: (i) they are naturally-occurring pigments with the desired color ranges; and, (ii) their role in nature is to absorb UV rays, and protect cells against UV light damage.

Based on those facts, an orally-ingested tanning agent containing a particular carotenoid called canthaxanthin (also spelled as canthaxanthine) was developed and marketed in a number of countries, under the trademark OROBRONZE™. It was a successful product for a number of years; however, after people had been using it for years, it was declared to be unsafe, and it was withdrawn and pulled off the market, because of an unanticipated side effect which became apparent only after years of use. This unwanted and dangerous side effect became evident because canthaxanthin crystals were being formed and deposited in the retinas of people who had been taking OROBRONZE capsules. That unwanted and dangerous side effect is described in various medical articles, including McGuinness et al 1985, Lonn 1987, and White et al 1988.

After canthaxanthin was declared illegal as a suntanning agent because of the retinal crystal problem, interest turned to β-carotene as a potential orally-ingested tanning agent (see, e.g., Mathews-Roth 1986 for a review), and at least one product, called BETATENE™, is being sold for that purpose (e.g., Stahl et al 1998). However, ever after years of use as an oral sun-tanning agent, it is not at all clear whether it works for that purpose, and if so, whether any value it may offer is accompanied or outweighed by unwanted risks and adverse effects. For example, as stated in Biesalski et al 2001, "most clinical studies have failed to convincingly demonstrate its beneficial effects so far . . . . Recent studies on skin cells in culture have revealed that β-carotene acts not only as an antioxidant but also has unexpected prooxidant properties. At present, there is an ongoing debate on the protective or potentially harmful role of β-carotene in human skin."

That reference to "pro-oxidant" properties needs special attention, because it indicates an alarming risk. Instead of reducing the damaging effects of oxidative free radicals, it appears that under at least some conditions, β-carotene may aggravate and worsen the types of damage that oxidative free radicals inflict on cells and biomolecules. This same warning was also contained in Eichler et al 2002, which stated, "The amounts of carotenoid needed for optimal protection [in certain types of cell culture tests, which used human fibroblast cells] were divergent at 0.05, 0.40 and 0.30 nmol/mg protein for lycopene, β-carotene and lutein, respectively. Beyond the optimum levels, further increases of carotenoid levels in cells led to pro-oxidant effects."

That warning signal raises serious questions, because it is impossible for people taking dietary supplements to know when they have reached, and when they have exceeded, the optimal or maximal levels that are safe, when cell culture conditions must be translated into practical advice concerning in vivo usage and dosages for humans. Accordingly, the warnings about β-carotene's "pro-oxidant" activity must be taken seriously, in view of the failure of β-carotene to offer any clear benefits with respect to preventing sunburns, in clinical trials on humans.

Along those same lines, it should also be noted β-carotene was recently discovered to pose a substantial health risk, relating to lung cancer and possibly other forms of cancer. In the mid to late 1990's, in three large and well-run multinational trials, it was discovered that daily ingestion of only 30 to 60 mg/day of β-carotene was enough to elevate the risk of lung cancer, among smokers, by factors approaching 30%. Those studies including the Beta Carotene and Retinal Efficacy Trial (CARET), done in the United States, and the Alpha-Tocopherol, Beta-Carotene Cancer Prevention Study (ATBC), done in Finland; they are reviewed in articles such as Goodman 2000. The risk-increasing dosage levels of β-carotene (30 to 60 mg/day) were only a small fraction of the recommended dosage levels of 180 mg/day, for people who were given β-carotene to treat skin diseases (see Mathews-Roth 1993). Therefore, those lung cancer data raise very serious questions about whether β-carotene can be taken safely, at the types of very high dosages that may be capable of provoking a significant darkening of skin tint.

In comparing zeaxanthin to β-carotene as a potential orally-ingested tanning agent, two additional factors should be noted. First, zeaxanthin (as well as lutein, canthaxanthine, and various other carotenoids) are classified as "non-retinoid" compounds, whereas β-carotene is a retinoid compound. The distinction between those two classes is that retinoid compounds are cleaved into two segments, and those two smaller molecules become Vitamin A, or similar molecules (which are generally classified as retinoid compounds). By contrast, "non-retinoid" carotenoids are not cleaved in that manner (at least, not in substantial quantities), and are not converted into Vitamin A or other retinoid compounds.

A second major factor which distinguishes zeaxanthin from β-carotene, as a skin tanning agent, centers on the effective dosage levels. As mentioned above, when people were given β-carotene to treat skin diseases such as porphyria, effective dosage levels of 180 mg/day were required. By contrast, among people taking zeaxanthin, dosages of only about one-sixth to about one-third of those levels (in the range of 30 to 60 mg/day) were required to induce substantial darkening of skin tint. Lower required dosages can lead not just to cost savings, but also to substantially higher margins of safety, and other benefits.

Some recent patents indicated that there is still interest in developing orally-ingested tanning formulations. U.S. Pat. No. 6,254,898 (Bragaglia 2001) discloses a mixture of green tea extract, lutein, lipoic acid, and selenomethionine, for use as an oral tanning agent. One of those ingredients, lutein, is a carotenoid. As mentioned in that patent, most of the plant sources (such as marigold flowers, which are bright yellow or orange) which are used to obtain commercial quantities of lutein also contain trace amounts of zeaxanthin; therefore, the tanning mixtures patented by Bragaglia referred to "lutein (zeaxanthin)".

U.S. Pat. No. 6,433,025 (Lorenz 2002) claimed the use of a different carotenoid, called astaxanthin, in orally-ingested tanning products. According to Lorenz, astaxanthin has roughly ten times the potency of other carotenoids (including castaxanthin, lutein, zeaxanthin, etc.) as an anti-oxidant protective agent.

Background Information on Zeaxanthin and Lutein

The subject invention focuses on zeaxanthin, a carotenoid which has been shown by the inventors herein to be useful as an orally-ingested tanning agent, when ingested at relatively high dosages in the range discussed below.

In the mid-1980's, it was discovered that zeaxanthin and lutein (their structures, which are very similar, are shown in FIG. 1) are the two carotenoids that are present in a small yellow-colored spot at the center of the human retina, called the macula.

Lutein can be obtained cheaply, in bulk, from marigold flowers, and it has been available for years. It is widely fed to chickens and to farm-raised salmon, since it helps create a darker and richer color to chicken skin, egg yolks, and salmon meat, which makes those pigmented products look fresher, healthier, and more appealing to purchasers and consumers. However, lutein tends to impart a yellow (rather than golden) tint to chickens and fish, when fed to them as a food additive. Therefore, lutein usually must be accompanied by at least one red-colored pigment, to allow the pigment mixture to impart a more desirable darker and richer golden tint to chickens and salmon.

Unlike lutein from marigolds, zeaxanthin has no simple and convenient plant source, and is present at only very tiny concentrations in natural foods. It also is very difficult to synthesize and purify. Therefore, zeaxanthin did not become commercially available to the public until 2002.

Because they are both known to be present in the human retina, and because they are both known to have UV-absorbing and anti-oxidant properties, lutein and zeaxanthin have recently begun to be advertised and sold as being potentially useful in helping treat or reduce the risk of a retinal disease called "macular degeneration", which is a leading cause of blindness among the elderly. Under the "DSHEA" law (an acronym for the Dietary Supplement Health and Education Act, passed by Congress in 1994), those types of sales are allowed under a set of rules that apply to "dietary supplements" which contain ingredients that already exist in foods and are part of the normal human diet. Since lutein and zeaxanthin both exist in spinach, corn, and certain other vegetables, they qualify for DSHEA (pronounced as "de-shay") treatment, and they are not regulated by the FDA under the types of strict standards that apply to drugs. However, because they have not undergone extensive testing in actual human clinical trials, lutein and zeaxanthin are prohibited by law from being labeled or advertised as having proven medical benefits. Under the DSHEA rules, the labels for lutein and/or zeaxanthin supplements are required by law to contain disclaimers such as, "These statements have not been evaluated by the Food and Drug Administration. This product is not intended to diagnose, treat, cure, or prevent any disease."

Before 2002, commercially available "mixed carotenoid" products that claimed to contain zeaxanthin contained only very small ("trace") quantities of zeaxanthin, and much higher concentrations of lutein. These lopsided ratios occur because, in nature, lutein is a much more dominant carotenoid, and is found in much greater quantities in most vegetables, and in other sources such as marigold flowers. As an illustration of the lopsided ratios, various sales brochures and other publications issued by the Kemin company (Des Moines, Iowa) for their FLORA-GLO™ brand of lutein from marigolds indicate that the ratio of lutein to zeaxanthin in their products are about 20:1 in favor of lutein.

However, in the early 1990's, various scientific findings began to suggest that the human retina (in particular, the macular portion of the retina, which is a yellow-pigmented spot at the center of the retina) appears to prefer zeaxanthin over lutein. This is evidenced by three factors: (i) the concentration of zeaxanthin is highest, and the concentration of lutein is lowest, near the very center of the macula; (ii) the fraction of lutein becomes higher, and the fraction of zeaxanthin decreases, around the outer portion of the macula; and, (iii) the macular portion of the retina apparently converts at least some of the lutein it receives into zeaxanthin (as noted below, it converts lutein into the S-R meso-zeaxanthin stereoisomer, which is not found in natural food sources). These factors are discussed in more detail in articles such as Bone et al 1985 and 1993.

One particular stereoisomer of zeaxanthin, referred to as the 3R,3'R isomer (or simply as the R-R isomer), is present in a number of food sources, including corn ("zea" is the Latin name for corn), and dark green vegetables such as spinach and kale. The R-R isomer became commercially available to the public only recently, starting in early 2002.

As described below, two other stereoisomers (known as the S-S isomer, and the S-R isomer which is also called meso-zeaxanthin) are also known, and the S-R isomer can be manufactured in commercial quantities, if desired, using lutein as a starting material. However, neither of those isomers are present in any significant quantity in any food sources, which raises questions over whether either of them can be sold to the public as dietary supplements under the DSHEA law, discussed above.

Despite its absence from food sources, the meso-zeaxanthin isomer is known to be present, in small quantities, in human retinas. Since it is not present in food sources, it is generally presumed and believed that meso-zeaxanthin, when found in the retina, is likely to be the result of enzymatic or possibly photo-activated chemical conversion of lutein into zeaxanthin.

If lutein, zeaxanthin, and other carotenoids (including β-carotene) are orally ingested in relatively high quantities, they compete against each other for uptake and transport through the intestinal walls and into circulating blood. This is presumed to be attributable to a carotenoid transport system, which can become saturated and unable to transport higher quantities of carotenoids through the intestinal walls and into the bloodstream. Therefore, if a mixture of zeaxanthin and lutein (or, presumably, zeaxanthin combined with β-carotene or any other carotenoid) is orally ingested, the presence of the lutein or other carotenoid will hinder and reduce the quantity of zeaxanthin which will reach and enter the circulating blood.

Because of certain apparent and presumed advantages of zeaxanthin over lutein, the first inventor herein has worked for more than a decade on the creation and commercialization of purified zeaxanthin (i.e., zeaxanthin which is free or essentially free of lutein, in a preparation that was not derived from a plant source). Among other things, he is the coinventor of five U.S. and numerous foreign patents on methods for making (and compositions containing) purified zeaxanthin, with little or no lutein present. Those U.S. patents include two patents (U.S. Pat. Nos. 5,308,759 and 5,427,783) which relate primarily to pigmented feed additives for poultry and farm-raised salmon, as briefly mentioned above, and three subsequent patents which relate to using zeaxanthin for medical purposes, in humans. Those three patents which relate to medical use in humans are U.S. Pat. No. 5,854,015 (on a method of making the purified 3R,3'R stereoisomer of zeaxanthin), U.S. Pat. No. 5,747,544 (on a method of using 3R,3'R-zeaxanthin to treat macular degeneration), and U.S. Pat. No. 5,827,652 (on zeaxanthin formulations for human ingestion). The contents and teachings of all five of those patents are incorporated herein by reference, as though fully set forth herein. That inventor is the founder of ZeaVision LLC (St. Louis, Mo.; www.zeavision.com), which began actively selling purified zeaxanthin in April 2002.

Several years ago, that inventor realized he had a unique opportunity to test zeaxanthin as a potential agent for preventing or reducing sunburn. He was already serving as one of the volunteers in a small-scale trial to measure zeaxanthin concentrations in circulating blood and retinal tissue, as a function of daily dosage levels, and he was planning a vacation trip to the Caribbean. He was aware of the problems (involving formation of canthaxanthin crystals in the retina) caused by the OROBRONZE product that had been pulled off the market some years earlier, and he realized that zeaxanthin probably would not cause similar problems, since it is naturally present in healthy retinas. Accordingly, he decided to begin taking a dosage of zeaxanthin (in the range of about 60 mg per day for roughly 2 weeks, increasing to about 80 mg/day for the week before the trip began) which began to cause a noticeable change in his skin color in a manner comparable to a mild suntan, just before leaving for his trip to the Caribbean.

During that trip, he noticed that he did not suffer any significant sunburns, even though he deliberately subjected himself to prolonged sessions of direct exposure to sunlight on a couple of occasions, at levels that would have caused serious sunburns during other times.

That trip provided the initial evidence showing that zeaxanthin, as a sole active agent and at a sufficient dosage which could begin to provoke a noticeable change in skin color, could serve as an effective way to prevent sunburn. However, the only supplies of purified zeaxanthin that were available at that time had come from lab-scale fermentation of the *F. multivorum* bacterial cells that are discussed below, in Example 1, and in the U.S. patents cited above.

Subsequently, as soon as adequate supplies of purified zeaxanthin became available for testing on other people, the inventor mentioned above discussed his own experiences, in using high-dosage zeaxanthin to prevent sunburns, with certain other individuals. Two of those people decided to try it, and their successful and positive reports (described in Examples 2 and 3) confirmed that purified zeaxanthin, when taken at relatively high dosages, is highly effective in helping prevent and reduce the severity of sunburns.

Subsequently, three individuals carried out another set of skin protection tests, using a medical-grade ultraviolet lamp to determine their "minimal erythemal dosage" levels. The medical term "erythema" refers to the type of reddening of the skin that typically occurs during sunburn (similar types of erythema also occur during inflammation of an injured or infected area). Therefore, in the context of testing for sunburn protection, the phrase "minimal erythemal dosage" (abbreviated as MED) refers to a quantity of UV exposure that will generate a reddened surface appearance, of the type that occurs when skin is sunburned. MED values can be expressed in terms of minutes of exposure, if a single lamp is used for a series of tests, and if each volunteer ensures that the distance between the UV bulb, and his/her skin, is held constant throughout the entire series of tests (this can be done with the required degree of accuracy by steps such as leaning one hip against a wall while the other hip is being exposed, and placing the lamp base at a marked and unchanging location on the floor).

Control (or baseline) tests were carried out, before each test subject began taking high-dosage zeaxanthin, on an area of skin on or near the buttock region (or on the inside of the forearm, which did not have a substantial base tan since these tests were being done during winter months). Baseline MED values for a certain region of skin on a certain individual can be determined by using a UV lamp in conjunction with a shield of heavy paper or light cardboard, through which holes roughly 1 cm wide were cut. Masking tape was used in some of the tests to cover the holes, and a dark-blue opaque masking tape was used, which is normally used by painters and construction workers to avoid damaging the painted or veneer finishes of cabinets. This type of masking tape uses a mild and non-aggressive adhesive, and the choice of this type of tape minimized any risk that pulling the tape off of a small area of skin might irritate the skin or provoke or aggravate a reddening response. In other tests, instead of peeling away masking tape, a ruler or strip of cardboard was used to either cover or expose additional holes at appropriate times.

Regardless of which type of covering device was used in conjunction with a shield, a series of small areas of pale skin that had not previously been exposed to sunlight were given progressively increasing exposure times, usually in increments of 30 seconds if exposures up to 10 minutes were used, and in increments of 60 seconds if exposures longer than 10 minutes were used. When a series of exposures was completed, the person removed the shield and then waited for 8 to 24 hours, to give the erythemal reaction enough time to develop fully.

When that region of skin was examined under a clear bright light, the small areas of skin that were exposed to UV radiation for the shortest time periods did not have any noticeable reddening. However, the areas of skin that were exposed for progressively longer periods of time became progressively redder, darker, and more distinct, as the sequence of exposure durations increased. The test subject identified a specific small patch of skin which had both (i) noticeable reddening, with reasonably clear and distinct edges or margins, and (ii) the shortest UV exposure duration of any patches that had become reddened in that manner. The time period which corresponded to that particular patch of skin was recorded, as the MED dosage for that person in that test. These time periods, expressed in minutes or portions thereof, provided usable and reliable indicators of MED values, and they could be generated conveniently, without requiring complicated and expensive equipment to measure the exact levels of incident radiation.

After a baseline (or "pre-ingestion") MED value was established for a test subject who had not been taking any zeaxanthin, that test subject then took a predetermined number of 10 mg capsules of zeaxanthin, each day, for a certain number of days. After that number of days, the person carried out a "post-ingestion" test, using the same sun lamp and the same procedures as used before, keeping all other factors constant.

In all of the people who participated in the UV lamp tests, at all dosage regimens tested (30 mg/day or higher), MED levels increased substantially. When the first inventor took 30 mg/day for 3 weeks, his MED increased from a baseline (pre-ingestion) level of 7.0 minutes, to a post-ingestion value of 10.5 minutes; when he then increased his dosage to 60 mg/day for another 3 weeks, his MED level increased even more, to 16 minutes. When the second inventor (who had previously taken 80 mg/day with no adverse effects) took 60 mg/day for 20 days, his pre-ingestion MED value of 5.0 increased to a post-ingestion value of 10. When a third volunteer took 50 mg/day for a single week, pre-ingestion MED value of 5.0 increased to a post-ingestion value of 7.3 (which was interpolated, since the skin area exposed for 7.0 minutes was nearly but not sufficient to qualify, while his 7.5 skin exposure appeared to be somewhat beyond a minimal qualifying level of redness).

These positive results, on three different test subjects who are all fairly large adult Caucasian males, consistently indicated that zeaxanthin dosages of 30 mg or greater did indeed decrease the vulnerability and susceptibility of skin to sunburning, and led to substantial increases in UV-exposure levels that were required to demonstrate any noticeable reddening of the skin.

It also should be noted that the first subject described above commenced taking high-dosage anti-oxidants, a number of weeks before his zeaxanthin regimen started. Therefore, any effect that those anti-oxidants may have had, in protecting his skin against UV damage, were factored into his baseline (pre-zeaxanthin) reading, and the increase in UV protection provided by the zeaxanthin regimen had to act on top of that.

Accordingly, one object of this invention is to disclose that zeaxanthin, when ingested at suitable dosages (such as about 5 mg/day for children, and 20 mg/day or greater in small and/or especially fair-skinned adults, and about 30 to 100 mg/day for a large adult), can provide highly effective protection against sunburns, even if no other tanning agents of any sort are used.

Another object of this invention is to disclose that zeaxanthin, when ingested at suitable dosages in a purified formulation where it is the sole or dominant carotenoid, can provide highly effective protection against sunburns.

A third object of this invention is to disclose that zeaxanthin, when ingested at suitable dosages over a span of several days, can provide effective protection against sunburns.

A fourth object of this invention is to disclose that zeaxanthin can be added, as an active agent, to orally ingested tanning formulations that may contain any other desired active agent, and the zeaxanthin will increase the efficacy of the oral tanning agent, if it is present at a suitable dosage.

A fifth object of this invention is to disclose that zeaxanthin can be included as an active agent in orally ingested tanning formulations, and it will provide significant ocular benefits, with no known risk of retinopathy or other ocular damage (as can be caused by other carotenoids), even when ingested in large dosages.

Another object of this invention is to disclose that zeaxanthin, when ingested at suitable dosages, can help protect the skin of at least some patients who suffer from abnormally high vulnerability to sunlight, such as among patients who are taking certain types of antibiotics or other pharmaceuticals, or patients who are suffering from a disease or syndrome such as albinism or porphyria.

Another object of this invention is to disclose that zeaxanthin, when ingested at suitable dosages, is likely to help reduce the incidence or severity of various types of unwanted skin discolorations or irregularities, such as skin blotching, splotching, or other irregular discolorations, and possibly the formation of severe and unwanted freckling and various other adverse conditions, in at least some patients.

These and other objects of the invention will become more apparent through the following summary and description.

SUMMARY OF THE INVENTION

A carotenoid substance called zeaxanthin, when ingested orally at suitable dosages such as 30 to 100 mg/day, can provide effective protection against sunburns. Zeaxanthin can also help sunburned and reddened skin be gradually converted into skin that appears to be completely healthy and tanned, rather than flaking or peeling off. A person who is anticipating a high level of sun exposure during approaching summer months, or during a vacation, business trip, golf or fishing outing, ski trip, or other travel or activity, can take a suitable dosage (such as about 30 to 100 mg/day) of zeaxanthin, for a span of roughly one to two weeks, prior to the anticipated high levels of sun exposure. In tests involving adults with relatively light-skinned complexions, it was found that zeaxanthin dosages of 30 to about 80 mg per day were sufficient to induce: (i) a mild but noticeable tinting, shading, or darkening of skin color, comparable to a mild suntan; (ii) a substantial increase in the person's ability to endure and withstand elevated levels of sun or UV exposure without any subsequent pain or discomfort, and without the subsequent peeling and flaking that characterizes most sunburns; and, (iii) an increased ability of reddened and sunburned skin to convert into intact skin that looks browned and healthily tanned.

A person can take oral zeaxanthin at suitable dosages for such purposes, in unit dosage formulations such as capsules or tablets, or in syrups or other liquid formulations, or as additives in various types of food preparations or substances that do not require high-temperature cooking. In this manner, zeaxanthin can be combined with controlled and/or supplemental exposure to direct sunlight or tanning lights, and/or combined with other active agents, such as dihydroxyacetone and/or tanning lotions or creams. This can reduce the amount of exposure to sunlight (or tanning lights) that will be required to achieve a desired level of tanning. In this manner, zeaxanthin can reduce the risks of skin cancer, premature aging, and similar problems.

Zeaxanthin can also provide preventive or therapeutic benefits among at least some patients who suffer from, or who are at elevated risk of, various other types of skin conditions, syndromes, or diseases. This includes patients who suffer from albinism, porphyria, or skin blotching or other lesions, and among patients taking certain types of antibiotics that increase their sensitivity to sunlight.

Since zeaxanthin is a potent anti-oxidant, and since it also has retina-protecting properties and appears to reduce the risk of a retinal disease called macular degeneration, oral ingestion of these dosages of a zeaxanthin, to enhance a tanned appearance and/or to protect against sunburn, premature aging and wrinkling of the skin, and skin cancer, is believed to pose no health risks, and instead can offer several health advantages, due to the anti-oxidant and retina-protecting activities of zeaxanthin.

This invention also disclosed capsules containing zeaxanthin in a range of about 30 to about 50 mg. These quantities are substantially higher than any capsules previously developed for other purposes, such as treating or preventing macular degeneration.

BRIEF DESCRIPTION OF THE DRAWINGS

FIG. 1 shows the chemical structure of zeaxanthin, along with beta-carotene and lutein for comparative purposes. Although the alternating single and double bonds are shown in fixed positions in these drawings, the electrons are actually in a "resonant" structure which is distributed across the entire straight-chain portions of these molecules, in a manner comparable to the electrons over a benzene ring. This allows these carotenoid molecules to absorb ultraviolet photons very efficiently, without destroying the molecules. It should be noted that zeaxanthin is symmetric, while lutein is not, and that lutein has two hydroxy groups on its end rings, while beta-carotene does not.

DETAILED DESCRIPTION

As summarized above, zeaxanthin, when ingested orally at relatively high dosages, has been shown to be effective in: (i) protecting against sunburns; (ii) causing a tinting of the skin in a manner that resembles a healthy and natural suntan; and, (iii) allowing sunburned and reddened skin to gradually convert to a healthy-looking tanned brown shade, rather than flaking or peeling off.

In addition, orally-ingested zeaxanthin also caused two other highly useful effects, when skin was tested using a medical-grade UV lamp, as described in Example 5. These tests were carried out in a manner which ensured that some small patches of skin, exposed to high-intensity UV radiation through the openings in a specialized shield that had been taped to the skin, would become seriously sunburned. The results of those tests clearly indicated, first, that the ingestion of about 60 or more mg of zeaxanthin per day led to "plateau effects", in which exposed patches of skin that received fairly long durations of UV exposure would reach a certain level of redness, but would not become significantly redder, even if exposed to substantially longer durations of light.

And second, the results of those tests also indicated that even if a patch of skin turned a fairly bright and intense shade of, red, following extended exposure to high-intensity UV light, that patch of skin would not blister, flake, or peel off during the following days. Instead, in volunteers who were taking more than about 50 mg of zeaxanthin per day, a red patch of UV-burned skin would be converted, over a span of roughly 1 to 2 weeks, into a brown patch with a healthy suntanned appearance, which strongly suggested the presence of increased levels of melanin (the dark brown pigment that appears in naturally suntanned skin) rather than zeaxanthin (a reddish-orange pigment).

Accordingly, stated in various alternate but consistent terms, this invention discloses that zeaxanthin (in sufficient dosages) can (i) reduce the risks of skin damage due to ultraviolet radiation; (ii) inhibit the adverse effects of ultraviolet radiation on the skin; and, (iii) increase skin tolerance to ultraviolet radiation. These types of skin damage and/or adverse effects that can be prevented or reduced by zeaxanthin include sunburn, premature aging or wrinkling associated with excess ultraviolet exposure, skin cancer (including melanoma or any other type of skin or cutaneous cancer), elevated risk of skin cancer, and skin lesions or uneven-pattern discolorations (including skin blotching, abnormally severe freckling, etc).

A purified form of zeaxanthin recently has become available to the public, from a company (ZeaVision LLC; www.zeavision.com) founded by the first designated inventor herein. It currently is sold in 10 mg capsules that can be ingested easily and conveniently. Accordingly, a person who is anticipating a high level of sun exposure during approaching summer months, or during a vacation or business trip that may involve golf, fishing, boating, skiing, sporting, or other outdoor activity or travel, can take from two to about ten of these capsules per day, for a span of roughly one to two weeks, prior to the anticipated high levels of sun exposure. Alternately or additionally, someone who wants to maintain a reasonably dark and suntanned skin tone throughout the course of the summer and into the fall can take from one to about five of these capsules per day, for as long as desired (including throughout the entire winter and spring seasons).

As used herein, references to "high dosages" and similar terms refer to any dosage of zeaxanthin that is about 20 mg or higher per day. Minimal effective dosages for skin-tinting or UV-protection use have not yet been carefully evaluated, and dosages as low as about 10 or 20 mg/day are anticipated to be capable of producing at least some detectable results (i.e., darker skin color and/or increased resistance to UV burning) in at least some people, including children and some adults with relatively pale skin. It is generally presumed that: (i) people who weigh less and/or have lower skin surface areas will likely show noticeable skin responses at lower dosage levels, compared to people who have more body mass and more skin surface; and, (ii) people who have light or very light complexions are likely to notice greater responses, in terms of more intense skin tinting and/or an increase in resistance to UV burning, than people who naturally have darker complexions.

Although dosages of only 10 to 20 mg/day may provide some benefits to some people, preferred skin-protecting dosages for adults heavier than about 60 kg (about 130 lbs.) start at about 30 mg/day, and extend up to about 100 mg/day. In tests involving several moderately large male adults with light or medium complexions, it was found that zeaxanthin dosages in a range of about 30 to about 80 mg per day were sufficient to induce: (i) a mild but noticeable darkening of skin pigmentation, comparable to a mild suntan; (ii) a substantial increase in the person's ability to endure and withstand elevated levels of sun or UV exposure without any subsequent pain or discomfort, and without the subsequent peeling and flaking that is characteristic of most sunburns; and, (iii) an increase in a person's ability to convert a reddened patch of skin, following high UV exposure levels, to a browned shade that appeared as a normal and healthy tan.

When considering preferred daily dosage ranges, the following general principles should be borne in mind:

1. A dosage level which induces a noticeable darkening or yellowing of the skin, in the palms of the hands and/or in one or more areas that are not normally exposed to sunlight, should be sufficient to provide at least some level of additional protection against sunburn;

2. A slight and mild yet clearly noticeable darkening of skin color can provide a good and useful way for a person to determine and use what will be, for that particular person, a safe and effective dosage of zeaxanthin that can provide increased sunburn protection;

3. Any person taking this product should be advised to use the normal precautions that are prudent whenever taking any new medicine. In most conditions, where rapidly accelerated tanning will not be necessary to avoid a sunburn, any person who begins taking it for the first time should start out with a dosage in a range of about 20 to 30 mg/day, and should continue that dosage for roughly a week before escalating to a higher dosage. Alternately, if someone learns that he or she will suddenly be subjected to dangerously high levels of sun, starting within a few days or a week, that person probably would be well-advised to start with a dosage of about 50 or 60 mg/day, before trying a higher dosage such as about 80 to 100 mg/day.

4. If a high dosage intended for skin tanning and/or sunburn protection leads to any noticeable adverse side effects, the person should stop taking it immediately, and if the adverse condition does not abate promptly, the person should consult a physician.

Accordingly, this invention also disclosed capsules or tablets containing zeaxanthin in a range of about 30 to about 50 mg. These unit-dosage quantities are substantially higher than any capsules or tablets previously developed for any other purposes, such as treating or preventing macular degeneration.

As used herein, "tablet" includes any solidified unit-dosage formulation that is homogenous, rather than encapsulated by a different layer of material. As is well known in the industry, tablets are typically formed by mixing an active agent with a so-called "binder" material that will take a fixed, specific, and durable shape when compressed to a suitable pressure in a mold. "Capsule" includes any unit dosage in which any type of distinct coating layer is used to encapsulate an active agent; this term includes conventional capsules, as well as so-called "soft-gel" capsules, and capsule-tablet hybrid forms (often called coated tablets, or "caplets") that include compressible binders but which are also coated with an outer layer (such as, for example, an enteric coating that will prevent degradation of a compound by stomach acids, and that will dissolve once the coated tablet reaches the intestines).

It should be noted that "unit dosage" formulations can also be provided in other manners, such as in individually-wrapped packets of a granular material, in a syrup or other liquid that has a known concentration of active agent and that is accompanied by instructions to take a certain volume of the liquid each day, etc.

Upper Dosage Limits

There is no known and specific upper limit to dosages of zeaxanthin that can be ingested safely. Based on tests done using lab animals, to determine whether any adverse effects could be detected at extremely high dosages, a "No Adverse Effect Level" (NOAEL) value of 1200 mg/day was reported to the U.S. Food and Drug Administration (US-FDA), by Roche Vitamins Inc. This value was subsequently made public by the US-FDA, in the "75-day Premarket Notification" for zeaxanthin, which was opened for public inspection by the FDA in June 2001, under docket number 95S-0316.

It should be recognized that NOAEL values do not state or imply that higher dosages would be injurious. Instead, a NOAEL value is merely a statement to the effect that an applicant company tested a certain compound up to a certain dosage level which is higher than the company anticipates using or recommending, and that the compound, when administered at that dosage level, did not cause any significant and observable adverse medical effects. In this regard, it should be noted that if an animal or human turns an abnormal and unnatural shade of an orange, red, or pumpkin color, that hyper-tinting effect is not regarded as an injurious medical effect for the purpose of calculating NOAEL levels, so long as the abnormal tinting will gradually recede and disappear after pigment ingestion is discontinued.

Accordingly, it is presumed (unless and until human clinical trials indicate otherwise) that levels of several hundred milligrams per day can likely be tolerated by humans, with no adverse medical effects other than potentially abnormal and undesired tinting of the skin in ways that do not resemble natural and healthy tans.

It should also be noted that high dosages of zeaxanthin tend to cause changes in fecal coloration, in humans. This is a reassuring factor, since it indicates that mammals can simply excrete zeaxanthin in their feces, if abnormally high dosages are ingested.

In view of the foregoing facts, it is recommended that anyone who wishes to take zeaxanthin for skin-tinting or skin-protection purposes should generally be advised to start with an initial dosage of about 30 to 80 mg/day, and stay at that initial dosage for at least a week or two before deciding whether to increase their ingestion levels to a higher dosage. It is also recommended by the inventors that no one should exceed a dosage of about 100 to 150 mg/day, unless they are under the supervision of a qualified physician.

Despite that warning and recommendation, it should be recognized that a second class of potential users is likely to want substantially higher dosages. This group includes people who are often referred to as "sun worshipers", who want to have a tan so dark that passers-by or strangers in a bar or restaurant will notice it quickly. The inventors herein will not speculate on maximal tolerable or safe dosage levels, for people who are determined to have the darkest skin possible regardless of elevated risks of skin damage. However, the inventors would point out that, among people who have chosen to pursue intensely dark tanning despite the known medical risks of accelerated wrinkling, aging, and skin cancer, ingestion of high dosages of zeaxanthin may well be able to render that type of potentially dangerous and wrinkle-accelerating tanning at least somewhat less dangerous, and less prone to premature aging and wrinkling, than exposure to prolonged direct sunlight, and with less danger than large dosages of canthaxanthine (which is still being sold over the Internet as a tanning agent, under a disclaimer which asserts that it is only being sold as a food coloring agent), tyrosine, β-carotene, or other orally-ingested agents that are known to be harmful in large dosages, or that remain unproven despite years of efforts to prove them effective.

Finally, it should be recognized that a third category of potential users also exists, who may want drastic results. This category includes people who, for legitimate reasons, wish to undergo a drastic darkening of their skin color, in a manner that will deliberately blur or minimize racial, ethnic, cultural, or other differences, such as for tourists, businessmen, missionaries, or diplomatic and military personnel who are visiting or stationed in a part of the world where Americans and/or pale-skinned people are resented, have difficulty doing business with the local population, or are at elevated risk of hostile activity. In such situations, extremely high dosages of zeaxanthin, combined with aggressive exposure to tanning beds or sunlight to stimulate melanin production, may be able to provide those types of results. However, any such efforts should not be undertaken except under the supervision of a qualified physician.

Use to Prevent Sunburns in Children

The use of zeaxanthin to provide skin protection among children deserves special attention, because studies have shown that children who suffer more than just one or two serious sunburns, while they are still young and growing, tend to suffer from higher rates of cancer, decades later. This is consistent with a number of other areas of medical concern, and it is consistent with what is known about genetics, genetic damage, and cancer. The general rule is that, if genetic damage is inflicted upon "fully adult" cells, in tissues that are no longer growing or reproducing actively and that have reached a "mere maintenance" level of reproduction, then the damage is likely to disappear when the cells gradually die out and are replaced by other cells. By contrast, if genetic damage is done to cells that are still involved in an active process of growing and reproducing (such as in a toddler or young child), the risks are much higher that any chromosomal abnormalities that may have been created in actively-reproducing cells will be passed on to subsequent progeny cells that descend from the damaged cells.

Effective dosages for toddlers and children have not yet been evaluated, but will deserve attention and analysis in the near future. For now, it is presumed that the preferred ranges of adult dosages, as discussed herein, should be decreased for toddlers and children in a manner that is roughly proportional to their body weight, compared to adult body weights. Accordingly, dosages of about 5 mg/day or higher are likely to provide noticeable skin tinting in toddlers and children who weigh about 10 to 25 kilograms (about 25 to about 60 pounds). Parents can monitor and supervise the process, and can ensure that their children are getting effective and useful dosages that will help protect against sunburns, by monitoring the tint of a child's skin, preferably with the aid of a color chart for comparison purposes. In general, as with adults, a preferred dosage is one that can generate a color change of at least 2 steps (also describes as increments, stages, etc.), when a skin color chart (as used by dermatologists) is used.

Accordingly, a vitamin-like compound that can be orally ingested, and that will help protect young children and even teenagers from severe sunburns, deserves careful attention, and offers a highly useful and valuable product. However, given the general reluctance of many children to eat vitamin pills (and the frequent failures of most parents to make sure their kids eat their vitamins every day), additional steps need to be taken, to provide maximal benefit from the ability of zeaxanthin to prevent sunburns among children and teenagers.

Therefore, this invention anticipates zeaxanthin as an additive in various types of food that are designed (which includes labeling, advertising, and other aspects of market segmenting) to appeal to, and to be ingested by, children and teenagers (collectively referred to herein as non-adults). Examples include various types of candy, cookies, cakes, pies, ice cream, and other sweetened foods that generally are regarded as treats, as well as hot dogs, lunch meats, chips, cheese preparations, pizza, cereal, and other salty, savory, or other foodstuffs that are deliberately targeted at market segments that specifically include large numbers of children and/or teenagers. Other candidate foodstuffs that are targeted at children and teenagers include gum, fruit juices and other types of flavored drinks (including sodas), and candy-fruit combinations (such as "Gummy Bears", "Fruit Rollups", etc.). Among babies, nearly any type of prepared baby food can be used, and preferred candidates would be those which already have a yellow, orange, or red color (such as sweet potatoes, bananas, etc.).

Preferred embodiments of these types of food substances include food substances that are targeted at non-adult market segments (this type of active "targeting" can be determined by evaluating the types of packaging and advertisements that are used to sell a food substance) which contain a quantity of zeaxanthin that is sufficient to cause a noticeable darkening of skin tint if a single helping of such food substance is ingested every other day. In general, food substances that have a reddish or orange color will usually be preferred for use as the carrier for zeaxanthin.

Timing of Ingestion; Oily Carrier Substances

A preferred regimen for ingesting oral zeaxanthin involves taking one or more zeaxanthin capsules or tablets along with a meal, or with a snack that contains a significant quantity of oil or fat. This is due to the fact that zeaxanthin (like most carotenoids) is relatively hydrophobic, and is not soluble in water. Therefore, its uptake through the intestinal walls and into circulating blood can be promoted and increased by the release of bile and certain pancreatic fluids secreted by the biliary system (which involves the liver, the pancreas, and the gall bladder). The release of those fluids, which help solubilize or emulsify hydrophobic compounds, normally occurs shortly after a food substance containing a significant quantity of oil or fat has been ingested. Accordingly, if desired, one way to ensure that this occurs can involve adding zeaxanthin to a food substance that contains at least one type of oil or fat.

One method that can be used to promote that goal involves formulating zeaxanthin in an oily carrier material, such as olive oil, corn oil, or other vegetable oils. If this approach is used, zeaxanthin can be sold at the appropriate dosages in watertight capsules (comparable to conventional capsules that contain Vitamin E), in a syrup-type liquid product or a chilled product such as yogurt or ice cream, in a product such as olive oil that is labelled and marketed for bread-dipping and similar uses, or in various other types of liquid products.

On the subject of zeaxanthin suspended in an oily carrier substance, it should be noted that methods for creating microcrystalline zeaxanthin, with extremely fine particle sizes (having submicron diameters) are disclosed in U.S. patent application Ser. No. 10/173,174, which has been assigned to ZeaVision LLC, the same assignee and owner herein. The contents of that application are incorporated herein by reference, as though fully set forth herein. The methods disclosed therein can be used to prepare a zeaxanthin formulation, suspended in an oily carrier, with improved bioavailability.

Even though the teachings herein disclose that purified zeaxanthin, by itself, can be used effectively for providing a tanning effect and preventing sunburns, it also should be recognized that zeaxanthin can be taken in combination with any other agent that may be able to provide an additive and/or synergistic effect, in terms of providing a darker tan and/or better protection against sunburns. Candidate agents that merit early evaluation in any such effort include various carotenoids that are normally present in the human diet, such as lutein, lycopene, and astaxanthin. Unlike canthaxanthin, which is not present in large quantities in the normal human diet and which led to problems of crystal formation in the retina when ingested at high dosages in the OROBRONZE product, various other carotenoids such as lutein, lycopene, and astaxanthin are present at substantial quantities in the normal human diet, and the human body therefore is believed well-equipped to handle them at any reasonable quantity. Lutein is present in numerous types of leafy green foods and in other vegetables; lycopene is present at fairly high concentrations in tomatoes and tomato products; and astaxanthin is present at fairly high concentrations in certain foods such as meat from salmon and tuna.

In addition, zeaxanthin at dosages of about 20 mg/day or higher can be combined with any other known or hereafter-discovered agent that is believed to be helpful in inducing a skin-darkening response when ingested orally. Such agents might include, as examples, melanocyte-stimulating hormone and analogs or active portions thereof, tyrosine, and/or any or all of the ingredients listed in U.S. Pat. No. 6,254,898 (Bragaglia 2001), which include green tea extract, lutein, lipoic acid, and selenomethionine.

It also should be recognized and understood that the method of this invention does not require rigid or rigorous adherence to a fixed daily schedule of taking a certain number of capsules per day. Instead, this method requires only that a sufficient quantity of zeaxanthin should be taken to cause an increase in either or both of the following: (i) a darkening of skin color or tint, in a manner and to an extent that is noticeable to the person taking the zeaxanthin, if used in conjunction with a skin color chart; and/or (ii) a increase in the skin's ability to withstand ultraviolet radiation without suffering erythema, in a manner and to an extent that can be detected using equipment and methods known to dermatology researchers (such as the MED or "minimal erythemal dosage" tests, as described in the Background section).

Because of various pharmacodynamic and "loading" factors, a preferred dosage regimen for achieving those two goals will involve daily ingestion of a reasonably consistent quantity of zeaxanthin (such as two or three capsules containing 10 mg each, on all or most days). Nevertheless, because of those same types of pharmacodynamic and "loading" factors, nearly any type of periodic and/or intermittent ingestion of zeaxanthin, in sufficiently high dosages, can achieve the same or similar overall results, by leading to the deposition of higher concentrations of zeaxanthin in the surface and/or near-surface layers of the skin.

Accordingly, various passages in this text and in the claims refer to "periodic or intermittent" dosages of zeaxanthin, in quantities sufficient to cause at least one of the two following effects: (1) a noticeable darkening of skin color, and/or (2) a measurable increase in the skin's ability to withstand ultraviolet radiation without suffering erythema.

In the first numbered phrase above, the term, "noticeable darkening of skin color," should be interpreted as being noticeable by an observant person with good vision who uses a printed color chart, to help evaluate and quantify any changes in skin coloration. Standardized skin color charts are available, and are used by dermatologists. Similar charts designed for use by the general public can be developed, in a manner comparable to color charts for teeth, which are sold publicly in kits that are marketed for over-the-counter tooth-whitening treatments. Accordingly, zeaxanthin which is sold for skin-darkening (i.e., artificial tanning) purposes can and preferably should be sold in packages that also contain skin color charts. In general, preferred dosages for skin protection purposes should be a daily dosage which, for a specific user, will induce a change in skin tint of at least two steps (or increments, stages, etc.), when post-ingestion skin tint is visually compared against pre-ingestion skin tint, using a printed color chart.

It should be recognized that printed color charts, although useful as a tool for measuring and quantifying the skin-darkening effects of zeaxanthin in any particular person, are not essential or necessary for carrying out the invention. Instead, in the various cases described in the examples, all of the volunteers who ingested 30 mg or more of zeaxanthin per day observed and reported darkened coloration in various areas of their skin (such as in the palms of the hands), even without the aid of any printed color charts.

The second phrase numbered above, referring to "measurable increase in the skin's ability to withstand ultraviolet radiation without suffering erythema", should be interpreted as being (i) detectable and measurable in quantitative terms, using equipment and methods known to dermatology researchers, and (ii) causing an increase which would be regarded by most skilled dermatologists as significant, rather than trivial, unproven, or failing to rise to a level of statistical significance. As one example of a significant increase, if three different measurements on a single person indicate that three different areas of skin which normally are covered by clothing have baseline (pre-zeaxanthin) MED levels which range from 4.5 to 5.0 minutes and which provide an average value of 4.8 minutes, when tested using consistent procedures and a specific UV lamp, and if periodic or intermittent ingestion of zeaxanthin by that same patient (regardless of how many pills he took on any particular day) raise his MED levels to a range of 5.0 to 5.5 minutes with an average value of 5.3 minutes (using the same procedures and the same UV lamp), most skilled dermatologists would conclude that the increase in MED for that patient was significant.

In this context, it also should be recognized that large numbers of measurements, in order to determine statistical significance, are not required. For example, if a single baseline measurement on a certain patient indicates an MED level of 5.0 minutes, and if periodic or intermittent ingestion of zeaxanthin by that patient (regardless of how many pills he or she takes on any particular day) increases his or her MED level to a higher number (such as 5.5 or more minutes), that increase should be regarded as a measurable and significant increase in his or her MED level.

For quantification purposes, some of the claims refer to MED increases of at least about 30%, when post-ingestion MED values (measured in minutes of exposure to a high-intensity UV lamp) are compared to pre-ingestion MED values. The 30% level is regarded as a "benchmark" standard of efficacy, for preferred dosages. That level was indeed surpassed by each of the volunteers who participated in the UV lamp tests described in the Examples.

It also should be recognized that specific and individual measurements, on a specific patient, are not required, if that patient is periodically or intermittently ingesting dosages of zeaxanthin which have already been reported to be sufficient to darken skin color and/or increase UV radiation resistance in significant numbers of other people, when such other people were tested objectively. As one example, if clinical trials are carried out to confirm this invention, and if the data from those clinical trials confirm that some particular dosage of zeaxanthin per day does indeed cause darkened skin color and/or increases resistance to UV radiation as an average result in most of the people who were tested, and if those results are published in a respectable scientific or medical journal, then that dosage will have been shown and reported to actually cause (i) a noticeable darkening of skin color, and/or, (ii) a measurable increase in the skin's ability to withstand ultraviolet radiation without suffering erythema.

Zeaxanthin Stereoisomers

Several factors should be noted about different sources and supplies of zeaxanthin, which can include various different stereoisomers of zeaxanthin.

Three different and distinct stereoisomers of zeaxanthin are known, and all three are included within the term "zeaxanthin" as used herein. As is known to any chemist, stereoisomers arise when a particular carbon atom (known as a chiral carbon atom) has four different atoms or groups bonded to it. When this happens, the four different groups can be bonded to that carbon atoms in either of two different spatial configurations. In general, if polarized light is passed through a purified stereoisomer which has been suspended or dissolved in a suitable liquid solvent, one of the stereoisomers of that compound will cause rotation of the polarized light in a rightward (or clockwise) direction; this isomer is usually referred to as the R (right) or D (dextrorotatory) isomer. The stereoisomer having the opposite configuration of groups attached to the chiral carbon atom will cause the rotation of polarized light in the opposite (leftward, or counterclockwise) direction; this stereoisomer is usually referred to as the L (left) or S (sinistra) isomer. Occasionally, one may also see references to "+" isomers (the "plus" isomers, which generally are the R/D isomers) and "−" isomers (the "minus" isomers, which generally are the L/S isomers); however, to avoid possible confusion between minus signs and hyphens, those types of references are not preferred, and nearly all articles which address the subject refer to zeaxanthin stereoisomers as being either R, or S.

Zeaxanthin has two different chiral carbon atoms, at the two positions known as the number 3 carbon atom, on one end ring, and the number 3' (pronounced three-prime) carbon atom, on the opposite end ring. Therefore, zeaxanthin can have any of three different stereoisomers. These three stereoisomers are: (1) the 3R,3'R isomer (also known as the R,R isomer, for convenience); (2) the 3S,3'S isomer (also known as the S,S isomer); and, (3) the 3S,3'R isomer (also known as the "meso" isomer, or as meso-zeaxanthin).

Because zeaxanthin is a symmetrical molecule, the 3S,3'R isomer and the 3R,3'S isomer are exactly identical to each other, and one can be converted into the other by merely flipping the molecule end-to-end. Therefore, rather than trying to nail down consistent references to either 3S,3'R or 3R,3'S zeaxanthin, most researchers and articles refer to the "mixed" or "half-and-half" combination simply as meso-zeaxanthin.

All zeaxanthin preparations that were tested as disclosed herein are believed to contain the 3R,3'R stereoisomer of zeaxanthin, as a sole or highly dominant stereoisomer. This is the isomer that is heavily dominant in nature; indeed, it is so heavily dominant, in naturally-occurring plants and bacteria, that the S,S and meso isomers are presumed to simply not exist in plants or bacteria. Accordingly, since the initial preparations that were tested by the first named inventor, as described in Example 1, were created by fermenting *Flavobacterium multivorum* cells, as described below, those zeaxanthin preparations were believed to contain essentially all R,R isomers, and essentially no S,R or S,S isomers.

However, the other zeaxanthin preparations that were tested in subsequent tests (as described in Examples 2-7) were created and purified by methods that involved chemical synthesis, rather than fermentation. Those preparations were believed to contain up to roughly 5% (by weight) of the S,R and/or S,S stereoisomers, as a byproduct of the synthesis and purification methods that were used. That low concentration of unwanted byproduct stereoisomers was reviewed by the U.S. Food and Drug Administration, and that agency did not take any steps to regulate or require any reduction in that level of byproduct isomers.

However, it should be noted that recently, certain companies (operating mainly outside the United States) have discovered that commercial quantities of meso-zeaxanthin can be created, by chemically treating lutein from marigold flowers. The companies doing that type of work have patented those processes and the resulting meso-zeaxanthin products.

It also should be noted that researchers have discovered that meso-zeaxanthin is present in human retinas. Since the meso isomer is not present in naturally-occurring foods, any meso-zeaxanthin that is detected in human or animal retinas is presumed to be a byproduct of certain naturally-occurring enzymatic (or possibly photoactivated) processes, which are believed to convert lutein into meso-zeaxanthin, inside the macula.

These factors raise serious questions about whether meso-zeaxanthin that has been deliberately manufactured in bulk quantities by treatment of lutein (as distinct from very small quantities of meso-zeaxanthin which are unavoidable byproducts of chemically synthesized zeaxanthin) can or should be approved for inclusion, as a "dietary supplement", in products intended for human consumption, under the terms of the Dietary Supplement Health and Education Act (DSHEA), briefly discussed above. Since the Patent Office has no authority or obligation to consider or resolve those issues, a patent filing is not the proper place to address those issues in any detail. Accordingly, the inventors herein simply state that both meso-zeaxanthin and S,S-zeaxanthin are intended to be included within the term "zeaxanthin", as used herein. Although the R,R isomer clearly is preferred for any human ingestion, and should comprise either the sole or at least the dominant isomer of zeaxanthin in any formulations sold to the public, meso-zeaxanthin and S,S-zeaxanthin are also covered by any claims or other passages herein that refer to zeaxanthin without specifying only the R,R isomer.

Zeaxanthin Esters

Most plants and many bacteria synthesize esters of zeaxanthin, lutein, and other carotenoids, instead of or in addition to so-called "free" carotenoids. Briefly, an ester is the type of molecule that is created when a hydrogen atom (which is part of one of the two hydroxy groups in the two end rings of zeaxanthin) is substituted by a certain type of relatively small organic molecule, in a manner which creates an ester bond.

When zeaxanthin esters are ingested by humans, most of the ester molecules will be broken apart, in a manner which will break the ester bond and release free (non-esterified) zeaxanthin molecules. This chemical reaction usually falls within a category of reactions called "hydrolysis", since a water molecule is effectively inserted into what was previously the ester bond. These reactions are catalyzed by enzymes generally known as "esterase" enzymes (since they break apart ester bonds). Although enzymatic cleavage of zeaxanthin esters does not occur at 100% efficiency, these reactions nevertheless comprise an important class of enzymatic reactions that occur readily within a human body, and these reactions will indeed release free zeaxanthin molecules, either in the gut or in the bloodstream, if zeaxanthin esters are ingested. Accordingly, the term "zeaxanthin" as used herein includes zeaxanthin esters.

Finally, any references to stereoisomers of zeaxanthin (such as 3R,3'R (or R,R) zeaxanthin, or meso-zeaxanthin) also include any stereoisomeric ester forms. In any zeaxanthin ester, the ester bonds that are coupled to the #3 and #3' chiral carbon atoms on the end rings of zeaxanthin will be in a spatial orientation that must be either the R or the S orientation, as described above under the heading "Zeaxanthin Stereoisomers."

Topical Formulations

If desired, zeaxanthin also can be added to any type of topical agent (such as a lotion, ointment, or cream) that is designed to be spread across a skin surface to create or enhance a tanned appearance. As mentioned in the Background section, agents which are used in such lotions and other topical formulas include dihydroxyacetone, erythrulose, and tyrosine. Such topical formulations can be used in conjunction with "systemic" (i.e., orally-ingested) tanning agents, including the zeaxanthin-containing oral formulations disclosed herein. If desired, any such topical formulation can also contain a permeation-enhancing agent (such as dimethyl sulfoxide, DMSO), to increase permeation of the zeaxanthin or any other ingredient into the epidermal tissue layers.

Apparent Zeaxanthin-Melanin Interactions

During the days and weeks that followed the UV-lamp tests described in Example 5, below, it was observed that, in areas of skin that clearly had been burned to a fairly dark reddened state by exposure to long durations of high-intensity UV radiation, those areas gradually converted to a clearly brown rather than red tint during the following days, over a span of roughly two weeks. This change in coloration, from clearly reddish to clearly brown, was so distinct and noticeable in that it has created, among the inventors herein, a belief that there is likely to be some type of active interaction(s) between zeaxanthin (a reddish pigment) and melanin (a dark brown pigment). This is not yet a certainty, and it cannot yet be supported by hard data, since no tissue biopsies have been carried out to determine the actual concentrations of zeaxanthin and melanin pigments in the various layers of the skin, following this type of treatment. Nevertheless, the visual results observed to date have been sufficiently clear, distinct, and noticeable to convince the inventors herein that some sort of interaction between zeaxanthin and melanin appears to be an active part of the biochemical processes that will occur if high-dosage zeaxanthin is ingested.

As examples of the types of interactive processes that may be involved and that should be studied, the interaction may involve some type of recruitment or activation process, where elevated zeaxanthin concentrations in the skin may help trigger or boost one or more cellular or molecular mechanisms that induce the synthesis of higher concentrations of melanin by affected cells.

Alternately or additionally, it may involve one or more processes of cellular survival or endurance, in which two or more steps occur in sequence, such as: (i) surface or near-surface skin cells that have been severely assaulted by lethal dosages of UV radiation will begin pumping out melanin, as a dying gesture, in order to help minimize damage in the lower epidermal layers; (ii) at least some of those upper-layer cells will be rescued and spared, by the anti-oxidant, UV-absorbing, or other protective properties of the zeaxanthin; and, (iii) the UV-stimulated cells which suffered a near-death experience will continue to pump out high quantities of melanin, because the production of melanin has no clear or abrupt turn-off switch, and instead tapers off or dies down only gradually.

As yet another biochemical mechanism that may be involved, zeaxanthin's anti-oxidant or other biochemical properties may help reduce the degradation of melanin after it has been synthesized by skin cells.

These potential types of interactions are only postulated, and biochemical analysis will be required to determine whether a true cause-and-effect relation exists between zeaxanthin supplements, and melanin responses. Nevertheless, it should be recognized that actual observations of the results that arose during the UV lamp tests convinced several observers that some sort of interaction probably did occur, which somehow tied together a zeaxanthin increase in the skin (due to ingestion of high-dosage supplements) with an increase in melanin production, in skin that was subjected to high-intensity UV radiation.

Accordingly, one of the methods disclosed herein for creating a darker tan and/or for protecting the skin against UV damage involves a two-step process: (i) ingesting zeaxanthin, at the dosages discussed herein; and, (ii) exposing at least one area of skin to ultraviolet radiation at a level which induces melanin production within the exposed area of skin. These two steps, if taken in combination, will create a combination of elevated zeaxanthin concentration (due to oral ingestion), and elevated melanin concentration (due to natural skin responses to UV light), in one or more epidermal layers in the exposed area of skin. That combination, of both elevated zeaxanthin and elevated melanin concentration in the skin or near-surface layers of the skin, can offer a better combination than either agent can provide by itself, of both desirable color which emulates a naturally suntanned tint, and highly effective protection against subsequent sunburns.

Claims that Include Labelling Limitations

This invention also relates to articles of manufacture, comprising: (i) ingestible formulations (such as capsules, tablets, syrups, or foodstuffs) that contain sufficient zeaxanthin to cause a noticeable darkening of skin color and/or a measurable increase in the skin's ability to withstand ultraviolet radiation without suffering erythema, provided that such formulations are enclosed within (ii) a package which contains, on the label, a printed statement which indicates to prospective purchasers that the zeaxanthin enclosed therein can be effective in causing a darkening of skin color in a manner which will resemble a suntan.

In this type of article of manufacture, which relies upon the printed label as one of the points of novelty, it should be noted and understood that: (i) the printed label is not being relied upon to establish patentability, and the invention as a whole includes, as an essential element, the tangible physical and chemical contents within the package; (ii) a number of decisions by the Court of Appeals for the Federal Circuit (and its predecessor) have explicitly stated that if printed matter is merely one item in an otherwise tangible and patentable article of manufacture, then the printed matter cannot be excised or deleted from the item before the Patent Office examines the claim; and, (iii) the laws and regulations that are enforced by the Food and Drug Administration, and that apply to such items of commerce, require that the contents and the label must be regarded as a single indivisible item of commerce. Accordingly, if the contents and the label are examined as a single item of commerce, as required by the FDA, then they meet and surpass all requirements for patentability.

EXAMPLES

Example 1

Initial Positive Result

The first named inventor's initial work in identifying and isolating a strain of bacteria which synthesize zeaxanthin as a sole carotenoid is described in U.S. Pat. Nos. 5,308,759 and 5,427,783, both invented by Gierhart. That work was carried out with the goal of obtaining a source of zeaxanthin, in bulk, for use as a pigment additive for chickens and farm-raised salmon. As mentioned above, when fed to poultry, either zeaxanthin or lutein will undergo an enzymatic conversion that leads to a deeper, darker, richer color for chicken skin and egg yolks, and when fed to farm-raised salmon, zeaxanthin leads to a deeper, darker, richer appearance of the meat. Both of those intensified colorations are appealing to consumers, since they make the resulting food products look fresher and healthier.

Lutein, which is obtained in bulk from marigold flowers, is currently used as the standard pigment additive for poultry and farm-raised salmon. However, this inventor suspected that zeaxanthin, which has certain advantages over lutein but which is much rarer in nature, might be more effective than lutein, if a reasonably pure source of zeaxanthin could be obtained at a reasonable price. Accordingly, inventor launched an effort to locate and isolate, from nature, a bacterial strain that could synthesize zeaxanthin. That effort succeeded, as described in U.S. Pat. Nos. 5,308,759 and 5,427,783. The strain of Flavobacterium multivorum that was shown to synthesize zeaxanthin was deposited with the American Type Culture Collection, and was given ATCC accession number 55238.

Some years later, the inventor realized, upon reading a scientific article, that zeaxanthin is one of the two carotenoid pigments (along with lutein) that create the yellow color of the macula, which is the extremely sensitive portion of the retina that is located at the exact center of the retina, directly above the location where the optic nerve connects to the eyeball. Upon learning that fact, and upon correlating it with various other items of information known to the inventor at that time (including knowledge about the UV-absorbing and anti-oxidant activities of carotenoids), the inventor realized that zeaxanthin might play a potentially important protective or other beneficial role in the macular portion of the retina. Accordingly, he commenced a series of follow-up activities to develop zeaxanthin into a product suited for human use.

One aspect of that project involved testing both zeaxanthin and lutein, in various dosages and formulations, to evaluate the increases that would result in circulating blood, and in retinal tissue, in human volunteers. A set of tests on human volunteers was developed with assistance by outside experts with skill and experience in that type of planning, and proper steps were taken to obtain informed consent from all volunteers. The inventor was an active participant in the zeaxanthin treatment arm of those studies. He ingested purified zeaxanthin at various dosage levels over a span of several months, and provided numerous blood samples that clearly established a valid dosage response in circulating blood concentrations.

At one point during those tests, after several relatively low dosages of purified zeaxanthin had been evaluated with no adverse effects of any sort, this inventor realized that an approaching vacation he was planning to take, to a Caribbean island during the month of February, offered a good opportunity to test purified zeaxanthin as a possible treatment to prevent or reduce the risk of sunburn.

Accordingly, he increased his daily dosage level to a point where a noticeable change in the color and tint of his skin began to appear, in areas that normally are not exposed to substantial direct sunlight (such as the inside portion of the arm). That dosage was in the range of about 60 mg of zeaxanthin per day for roughly 2 weeks, then about 80 mg/day for a week). During that time, even though he was planning a trip to the Caribbean, he did not visit any tanning salons, and did not make any effort during those winter months to obtain a "base tan" that could provide some additional protection against sunburn.

While in the Caribbean, he intentionally exposed himself to direct sunlight at a substantially higher intensity than he normally received in his home state of Missouri, for sufficient periods of time to give him an "onset" type of sunburn, which would convert to a suntan over a span of several days if he took proper care of his skin and put lotion on it. However, he noticed that he did not get sunburned in the normal manner, despite the higher level of sun exposure. Instead, any mild redness he experienced in the evening, at the end of a day with a prolonged session in the sun, was not accompanied by sensations of pain, burning, tightness, or dryness in the skin, and it converted to a normal (or slightly reddish, but not uncomfortable) suntan within less than 24 hours.

These differences in responses by his skin were sufficiently unusual that they were clearly noticed by him, at the time. However, there was not a sufficient supply of purified zeaxanthin to repeat the test on any one else. Therefore, he continued on the path toward scale-up, manufacturing, and commercialization of purified zeaxanthin. As soon as a sufficient quantity of purified zeaxanthin was available in capsules having known and controlled dosages, he discussed the above-described experiences with several coworkers, who chose to carry out their own tests to see whether they would get the same results.

Example 2

First Confirmatory Experience by Coworker

In April 2002, a company (ZeaVision LLC, located in St. Louis, Mo.) founded by the first-named inventor began selling purified zeaxanthin in 3 mg and 10 mg capsules, primarily through its website (www.zeavision.com). During the startup phase, bottles of 10 mg capsules were given to a number of people who had played important roles in helping get the company started.

The first-named inventor talked with several coworkers who happened to have light skin complexions and blue or green eyes, all of whom are prone to sunburn. At various times, the inventor discussed with those coworkers a number of factors, including (i) his experience on his Caribbean trip, (ii) dosage and safety data (including the 1200 mg/day "no adverse effect level" that had been reported to the U.S. Food and Drug Administration by Roche Vitamins, as mentioned in the Background section; and, (iii) the effects of zeaxanthin compared to lutein, on the color of chicken skin when either compound was fed to chickens.

After considering those and other discussions, some of the first inventor's coworkers decided to try sunburn-related tests on themselves, using elevated dosages of zeaxanthin, either as the summer season approached, or as more information became available during the summer.

One coworker, a male in his 30's, began taking 10 mg/day during April, and increased to 20 mg/day during May, and then increased to 40 mg/day during June. At the 40 mg dosage, he began to detect a slight but noticeable darkening of his skin, toward a color that he found pleasing and described as a "golden tan" color. In July, he increased his dosage to 80 mg/day during several week-long periods, to see what effect it would have on skin color, and on sunburn resistance. His skin color turned noticeably darker, once again in a manner which he regarded as pleasing and described as a "golden tan" color.

On a couple of weekend days during July, and during a family vacation in early August, he deliberately subjected himself to prolonged sun exposure without any sun-blocking lotion, including sessions that normally would have caused him substantial or severe sunburns accompanied by serious discomfort. Instead of receiving those types of sunburns, by the evening of a day like that, he could detect some redness in his skin color, and a heightened condition of skin sensitivity; however, he felt no serious discomfort or sense of "radiating heat" in his skin, and no interference with his ability to sleep comfortably; in addition, by the following day, the redness appeared to be entirely gone. In his opinion, the zeaxanthin provided both (i) excellent protection against sunburn, and (ii) a darkened skin color, which he enjoyed and regarded as an entirely satisfactory and pleasing look of someone who has a good suntan.

Example 3

Second Confirmatory Experience

After seeing and hearing the highly positive results obtained by the two people described in Examples 1 and 2, another coworker, a male in his 50's, decided to also begin taking zeaxanthin at 40 mg/day, starting a couple of weeks before going on a summer vacation with his family. His skin turned a mildly darker and more tanned shade, before he left.

Upon returning from his vacation, he reported that he had not suffered any sunburns, despite a couple of sessions of prolonged sun exposure, with no protective lotion, that normally would have resulted in sunburns for him. Even after he deliberately subjected himself to prolonged sun exposure sessions that normally would have resulted in a sunburn, he reported that there was a slightly heightened sensitivity in a couple of areas, mainly on his forehead and face, but there were no feelings of significant pain or discomfort, and no difficulty sleeping, and by the next morning any redness had turned into what appeared to be a normal and healthy suntan.

Example 4

Lack of Sunburn Protection at 10 Mg/Day

A third coworker, a male in his 50's, began taking 10 mg of zeaxanthin per day. Although he was aware of the above-described anecdotal reports of sunburn protection being provided by higher dosages, he decided to not alter his dosage, and he stayed at a dosage of 10 mg/day. He reported that, during a family vacation, he suffered a noticeable sunburn after a prolonged session of exposure to the sun, and he indicated that he had not detected and could not detect any change in his skin color, or any change in his sensitivity to sunburn.

Accordingly, the three positive reports listed in Examples 1-3, and the negative "control" test by a person who took only 10 mg/day, were entirely consistent, and indicated that when zeaxanthin is taken at a dosage that is higher than 10 mg per day, over a span of about 2 weeks or longer, it can significantly improve and enhance the ability of a person to withstand prolonged exposure to direct sunlight, with reduced risk of a sunburn.

Example 5

Tests using Ultraviolet Lamp

After assessing the results of the tests described above, the inventors herein realized that the tests described above were all prone to some degree of subjectivity, since they reported impressions and beliefs rather than quantified data. Accordingly, they embarked on an additional effort to determine whether and how they could gather objective and impartial data, within a limited budget and without requiring full-scale human clinical trials.

After consulting with some dermatologists, they settled upon a method of using a medical-grade UV lamp, which could be purchased at reasonable expense and then used any number of times, to determine "Minimal Erythema Dosage" (MED) levels. This type of measurement, which has been used many times in numerous clinical trials, is discussed in the Background section.

Briefly, a person doing this type of test tapes a heavy paper shield, with small holes in it, onto an untanned area of skin, such as around the hip or buttocks; or, if the test is being done during the winter months, this test can also be done on the untanned inner side of the forearm. An additional masking device (such as dark masking tape, or a strip of cardboard) is used, and is moved or altered in a progressive manner, so that the small areas of skin that are exposed through the holes in the shield will be exposed to progressively greater levels of UV radiation, from the UV lamp. The small area of skin which had the lowest duration (in minutes) of UV exposure, and yet which turned noticeably red with clear margins, corresponded to the MED value for that person, on that day. By carrying out a "pre-ingestion" MED test before any zeaxanthin was ingested, and by comparing that MED value against a "post-ingestion" MED value from the same person after a number of days of ingesting 30 mg or more of zeaxanthin per day, a comparative, impartial, and objective assessment could be obtained, to determine whether the zeaxanthin regimen caused an increase in the skin's resistance to burning.

To carry out these tests, a Sperti medical-grade UV lamp was purchased. It was rated at 800 watts of UV light, with 60-70% of the UV radiation in the "UV-A" part of the spectrum, and 30-40% of the UV radiation in the "UV-B" part of the spectrum. The three volunteers who did these tests discussed and shared their experiences with each other, to help ensure that their approaches and methods were similar and consistent. All three volunteers stood as motionless as possible (such as with one hip or forearm pressed against a wall), and placing the lamp a fixed distance away, using the short edge (8.5 inches) of a sheet of typing paper to provide a convenient method of establishing a proper and consistent distance. The lamp had a timer with a visible counter, and it shut off automatically when a test period finished.

The first named inventor (the same person who had detected a protective effect of zeaxanthin during a previous trip to the Caribbean, as described in Example 1) determined an exposure of seven minutes as his pre-ingestion MED value. He had refrained from taking any zeaxanthin for three months before the test. However, during that period, he took a daily multivitamin, which contained 100% of the recommended daily allowances for the standard set of vitamins, as well as two "Protegra Anti-Oxidant" softgel capsules as well, because Protegra contains high levels of various known anti-oxidants (including daily dosages as follows: β-Carotene, 10,000 I.U.; Vitamin C, 500 mg; Vitamin E, 400 I.U.; selenium, 30 micrograms; copper, 2 mg; manganese, 3 mg; and zinc, 15 mg). This high level of anti-oxidant ingestion was intended to ensure that any protective effects of zeaxanthin would need to extend over and above any protective effects that might be caused by either β-carotene, or other anti-oxidants.

The results of this person's pre-ingestion test indicated an MED value of 7.0 minutes (with exposure intervals of 30 seconds). This baseline value was confirmed on both the forearm and the buttocks. Inspections were done at 8 hours, 24 hours, and 48 hours, and did not appear to change significantly over that time span.

Promptly after that baseline determination, this person began ingesting 30 mg of zeaxanthin per day (10 mg with his morning meal, and 20 mg with his evening meal, using the 10 mg capsules available from ZeaVision LLC). During that time, he continued to take the same anti-oxidant regimen as before. After three weeks of zeaxanthin ingestion at 30 mg/day, there was a slightly perceptible color change in the palms of the hands when examined in clear bright light; however, it was not easily perceivable in the test skin areas. He then re-tested himself, using the same UV lamp and procedures as before. His MED values, after 3 weeks of taking 30 mg/day of zeaxanthin, increased his baseline value of 7 minutes, up to 10.5 minutes.

This same person then increased his dosage of zeaxanthin to 60 mg/day, for another 3-week span. He then tested himself again, using the same UV lamp and procedures. His MED level in that test increased to 16 minutes, which was more than double his baseline value of 7.

Another volunteer (the same person described in Example 2) carried out a similar set of tests, using the same lamp, and using conditions modelled closely on the first person's experiences. This volunteer generally has a lighter complexion than the first subject, and is more prone to sunburns, and did not take any other anti-oxidants either before or during his test period. His baseline test, before any ZX ingestion, gave an MED value of 5.0 minutes. Subsequently, after taking 60 mg/day of zeaxanthin for 20 days, his MED value doubled, to 10.

In addition, both of these two test subjects noticed certain additional results, involving the small patches of clearly sun-burned areas of skin that were created by their post-ingestion tests (these small areas of skin were the exposed areas that received high-intensity UV radiation for substantially longer periods than the MED duration). Both test subjects noticed that their clearly UV-burned spots did not begin peeling or flaking after several days; instead, those spots did either of two things, depending on how badly burned they were. Spots that were burned only mildly either faded into the background skin color within a day or two, or they gradually converted into a natural and healthy-looking shade of brown, which emulated a natural suntan, over a span of roughly 1 to 2 weeks. Spots that were more severely burned usually converted into a natural and healthy-looking shade of brown, which emulated a natural suntan, over a span of roughly 1 to 2 weeks or somewhat longer.

In addition, both of these test subjects also noticed another effect, after ingesting zeaxanthin. Even though they subjected a number of small patches of skin to fairly long sessions of high-intensity UV light (up to durations that exceeded 20 minutes, in the first subject discussed, and up to 15 minutes, in the second subject), the longest-duration patches of skin did not become any redder or more uncomfortable than the other patches that had been exposed to somewhat shorter durations. In other words, the zeaxanthin apparently created a "plateau effect", which protected their skin against more severe burning.

Another volunteer decided to try a dosage of 50 mg/day for a single week, to determine whether someone could substantially boost his resistance to sunburn within 7 days. Not realizing that zeaxanthin is ingested more readily if eaten with a meal, he took 5 capsules per day at irregular periods, separated by at least 2 hours between successive capsules. His baseline MED level was 5.0, and his MED level after 7 days of taking zeaxanthin increased to between 7.0 and 7.5 (interpolated to be about 7.3).

Accordingly, all 3 of these test subjects experienced substantial increases in their MED values. In addition, as mentioned above, the zeaxanthin also appeared to have other beneficial effects, including: (i) improved conversion of UV-burned areas of skin into browned and apparently tanned areas; and, (ii) a "plateau effect", which caused the intensity of burning and reddening to level off at a moderate level, even in areas of skin that received substantially longer durations of high-intensity UV radiation.

Clearly, the reports listed above are preliminary, and need to be followed up with more controlled research that can evaluate the limits and parameters of zeaxanthin's ability to do any or all of the following: (i) protect against sunburns; (ii) help create or enhance, either by itself or in conjunction with controlled amounts of sun exposure, other carotenoids, and/or other active agents, a darkened skin color which will appear as a healthy and natural suntan; and/or (iii) reduce the risk or severity of skin cancer, skin discoloration (such as mottling, "liver spots", etc.), and other skin problems. Such tests can be done either among the general population (presumably excluding people who already have skin that is sufficiently dark that they would not normally desire darker skin through suntanning), or they can be limited to selected groups or classes of people, such as people who are exceptionally fair-skinned and at high risk of sunburns, people who have suffered multiple sunburns in the past, people who have already been treated for skin cancer, people who suffer from unusual numbers of liver spots, mottling, or other skin discolorations, etc.

In addition, more research can be carried out, if desired, on whether combinations of zeaxanthin with one or more other carotenoids (such as lutein, lycopene, astaxanthin, beta-carotene, etc.) and/or other ingredients (such as melanocyte-stimulating hormone and any analogs or active fragments thereof, tyrosine, dihydroxyacetone, erythrulose, or anti-oxidants such as Vitamin E and other tocopherols, selenium, etc.), applied in either oral or topical form, may be able to provide better responses than zeaxanthin by itself, in terms of protecting the skin against overexposure to the sun, and/or in providing a desired cosmetic darkening of the skin which will resemble a suntan.

Although more research is needed in testing zeaxanthin in combination with other candidate active agents, and in fine-tuning the preferred dosage levels of zeaxanthin for different people, different skin types, etc., it should be recognized and understood that the anecdotal reports described above are all entirely consistent, and point to a highly useful invention and treatment. These initial results strongly indicate that, for at least some people, ingestion of higher than 10 mg or more of zeaxanthin per day (and preferably in the range of at least about 20 or 30 mg/day, up to about 80 to 100 mg/day) can provide a substantial and highly useful and beneficial form of protection against sunburn, and may also provide a useful, healthy, and desirable agent for allowing people to achieve a desirably suntanned appearance, with less exposure to direct sunlight, and with lower risks of skin cancer and premature aging of the skin.

This invention also discloses a method of inhibiting a skin-hypersensitivity side-effect of a therapeutic drug which induces skin-hypersensitivity (such as quinoline antibiotics). This method comprises the step of ingesting at least about 10 mg of zeaxanthin per day, while the therapeutic drug is being taken. If desired, the zeaxanthin can be packaged in the same capsule, tablet, liquid, or other formulation with the therapeutic drug.

Thus, there has been shown and described a new and useful agent that can be orally ingested, to help safeguard the skin against sunburns and future risks of skin cancer and other problems. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

REFERENCES

Biesalski, H. K., et al, "UV light, beta-carotene and human skin—beneficial and potentially harmful effects," *Arch Biochem Biophys* 389: 1-6 (2001)

Bone, R. A., et al, "Preliminary identification of the human macular pigment," *Vision Res.* 25: 1531-1535 (1985)

Bone R. A., et al, "Stereochemistry of the macular carotenoids," *Invest Ophthalmol Vis Sci* 34: 2033-2040 (1993)

Eichler, O., et al, "Divergent optimum levels of lycopene, beta-carotene and lutein protecting against UVB irradiation in human fibroblasts," *Photochem Photobiol* 75: 503-6 (2002)

Goodman, G. E., "Prevention of lung cancer," *Crit Rev Oncol Hematol* 33: 187-97 (2000)

Lee J., et al, "Carotenoid supplementation reduces erythema in human skin after simulated solar radiation exposure," *Proc Soc Exp Biol Med* 223: 170-4 (2000)

Lonn, L. I., "Canthaxanthin retinopathy," *Arch Ophthalmol* 105: 1590-1 (1987)

McGuinness, R. et al, "Gold dust retinopathy after the ingestion of canthaxanthine to produce skin-bronzing," *Med J Aust* 143: 622-3 (1985)

Mathews-Roth, M. M., "Carotenoids quench evolution of excited species in epidermis exposed to UV-B light," *Photochem Photobiol* 43: 91-3 (1986)

Mathews-Roth, M. M., "Carotenoids in erythropoietic protoporphyria and other photosensitivity diseases," *Ann N Y Acad Sci* 691: 127-38 (1993)

Offord, E. A., et al, "Photoprotective potential of lycopene, beta-carotene, vitamin E, vitamin C and carnosic acid in UVA-irradiated human skin fibroblasts," *Free Radic Biol Med* 32: 1293-303 (2002)

Stahl, W., et al, "Increased dermal carotenoid levels . . . in women ingesting Betatene," *J Nutr* 128: 903-907 (1998)

White, G. L. et al, "Retinal crystals and oral tanning agents," *Am Fam Physician* 37: 125-6 (1988)

The invention claimed is:

1. A method of providing increased sunburn protection to the skin, comprising:

ingesting, over a period of time, at least 10 milligrams per day of zeaxanthin, the ingested zeaxanthin being in an oral formulation that is one of a group consisting of a capsule, a tablet, and a liquid, the zeaxanthin in the oral formulation being predominantly present in the form of the R-R stereoisomer of zeaxanthin; and during the period of time, applying a topical formulation to the skin so as to darken the skin, the topical formulation being in the form that is one of a group consisting of a lotion, an ointment, or a cream, the topical formulation including zeaxanthin.

2. The method of claim 1, wherein the oral formulation provides at least about 20 milligrams per day of zeaxanthin.

3. The method of claim 1, wherein the topical formulation includes a permeation-enhancing agent to increase permeation of the zeaxanthin from the topical formulation into epidermal tissue layers of the skin.

4. The method of claim 3, wherein the permeation-enhancing agent is dimethyl sulfoxide.

5. The method of claim 1, wherein the zeaxanthin is present in the oral formulation in an oily carrier substance.

6. The method of claim 1, wherein the oral formulation includes at least one second active agent, the second agent is selected from the group consisting of melanocyte-stimulating hormone and analogs, non-zeaxanthin carotenoids, tyrosine, green tea extract, lutein, lipoic acid, and selenomethionine.

7. The method of claim 6, wherein the zeaxanthin is the predominate carotenoid in the oral formulation.

8. The method of claim 6, wherein the topical formulation further includes at least one of dihydroxyacetone, erythrulose, and tyrosine.

9. The method of claim 1, wherein the ingesting, by itself, causes a darkening of the skin.

10. The method of claim 9, wherein the darkening of the skin from the ingesting darkens the skin by at least two color shades when measured using a dermatologist skin chart.

11. The method of claim 1, wherein the zeaxanthin is the predominate carotenoid in the oral formulation.

12. The method of claim 11, wherein the oral formulation further includes lutein.

13. A method of providing increased sunburn protection to the skin, comprising:

ingesting, over a period of time, at least 10 milligrams per day of zeaxanthin, the ingested zeaxanthin being in an oral formulation that is one of a group consisting of a capsule, a tablet, and a liquid, the zeaxanthin in the oral formulation being predominantly present in the form of the R-R stereoisomer of zeaxanthin, the zeaxanthin is the predominate carotenoid in the oral formulation; and during the period of time, applying a topical formulation to the skin so as to darken the skin, the topical formulation being in the form that is one of a group consisting of a lotion, an ointment, or a cream, the topical formulation including zeaxanthin and a permeation-enhancing agent to increase permeation of the zeaxanthin from the topical formulation into tissue layers of the skin.

14. The method of claim 13, wherein the oral formulation provides at least about 20 milligrams per day of zeaxanthin.

15. The method of claim 14, wherein the oral formulation further includes lutein.

16. The method of claim 13, wherein the permeation-enhancing agent is dimethyl sulfoxide.

17. The method of claim 13, wherein the topical formulation further includes at least one of dihydroxyacetone, erythrulose, and tyrosine.

* * * * *